US011493660B2

(12) United States Patent
Matsuoka et al.

(10) Patent No.: US 11,493,660 B2
(45) Date of Patent: Nov. 8, 2022

(54) INSPECTION DEVICE

(71) Applicant: CANON DENSHI KABUSHIKI KAISHA, Chichibu (JP)

(72) Inventors: Takahiro Matsuoka, Saitama (JP); Masahiro Kawase, Saitama (JP)

(73) Assignee: CANON DENSHI KABUSHIKI KAISHA, Saitama (JP)

( * ) Notice: Subject to any disclaimer, the term of this patent is extended or adjusted under 35 U.S.C. 154(b) by 152 days.

(21) Appl. No.: 16/966,525

(22) PCT Filed: Jan. 31, 2019

(86) PCT No.: PCT/JP2019/003451
§ 371 (c)(1),
(2) Date: Jul. 31, 2020

(87) PCT Pub. No.: WO2019/151422
PCT Pub. Date: Aug. 8, 2019

(65) Prior Publication Data
US 2021/0055445 A1 Feb. 25, 2021

(30) Foreign Application Priority Data
Jan. 31, 2018 (JP) .............................. JP2018-014798
May 9, 2018 (JP) .............................. JP2018-090774

(51) Int. Cl.
*G01N 27/72* (2006.01)
*G01R 33/12* (2006.01)
(Continued)

(52) U.S. Cl.
CPC .............. *G01V 3/08* (2013.01); *G01N 22/00* (2013.01); *G01N 22/04* (2013.01); *G01N 27/72* (2013.01);
(Continued)

(58) Field of Classification Search
CPC .......... G01V 3/08; G01N 27/72; G01N 27/82; G01N 27/9046; G01N 27/9006; G01R 33/12; G01R 33/1215
(Continued)

(56) References Cited

U.S. PATENT DOCUMENTS

| 6,456,068 B1 | 9/2002 | Kawase |
| 2002/0047701 A1 | 4/2002 | Kawase |

(Continued)

FOREIGN PATENT DOCUMENTS

| JP | 3819903 B2 | 9/2006 |
| JP | 5069162 B2 | 11/2012 |

(Continued)

OTHER PUBLICATIONS

English translation of Apr. 16, 2019 International Search Report dated Aug. 4, 2020 International Preliminary Report on Patentability for International Patent Application No. PCT/JP2019/003451.

*Primary Examiner* — Raul J Rios Russo
(74) *Attorney, Agent, or Firm* — Venable LLP

(57) ABSTRACT

The inspection device includes: a conveyance route that conveys an inspection object at moving speed v; a first magnetic detector and a second magnetic detector that detect a magnetic field of a magnetic foreign object contained in the inspection object; an amplifying unit that amplifies detection signals of the first magnetic detector and the second magnetic detector; and a computation processing unit that performs processing of multiplying the detection signal of the second magnetic detector by a signal obtained by delaying the detection signal of the first magnetic detector. The first magnetic detector and the second magnetic detector each include one magnetic sensor and the magnetic sensors form a pair.

24 Claims, 27 Drawing Sheets

(51) Int. Cl.
*G01V 3/08* (2006.01)
*G01N 22/04* (2006.01)
*G01N 22/00* (2006.01)
*G01N 33/28* (2006.01)
*G01R 27/04* (2006.01)
*G01R 25/04* (2006.01)
*G01R 27/22* (2006.01)
*G01N 27/82* (2006.01)
*G01N 27/90* (2021.01)

(52) U.S. Cl.
CPC ......... *G01N 27/82* (2013.01); *G01N 27/9006* (2013.01); *G01N 27/9046* (2013.01); *G01N 33/2823* (2013.01); *G01R 25/04* (2013.01); *G01R 27/04* (2013.01); *G01R 27/22* (2013.01); *G01R 33/12* (2013.01); *G01R 33/1215* (2013.01)

(58) Field of Classification Search
USPC ..................................... 324/51, 55, 200, 228
See application file for complete search history.

(56) References Cited

U.S. PATENT DOCUMENTS

| | | |
|---|---|---|
| 2003/0164766 A1 | 9/2003 | Britton |
| 2004/0008026 A1 | 1/2004 | Kawase |
| 2004/0046550 A1* | 3/2004 | Kondo ................... G01N 27/82 324/234 |
| 2004/0201374 A1 | 10/2004 | Kawase |
| 2005/0206373 A1* | 9/2005 | Kondo ................... G01N 27/82 324/239 |
| 2006/0226833 A1* | 10/2006 | Kubotera ............... G01V 3/105 340/551 |
| 2012/0326716 A1 | 12/2012 | Kawase |
| 2014/0375305 A1 | 12/2014 | Kawase |
| 2020/0116802 A1 | 4/2020 | Matsuoka et al. |

FOREIGN PATENT DOCUMENTS

| | | |
|---|---|---|
| JP | 5695428 B2 | 4/2015 |
| JP | 2016-217946 A | 12/2016 |
| JP | 6121689 B2 | 4/2017 |

* cited by examiner (a)

(b)

(a)

(b)

(c)

(d)

(a)

(b)

(c)

INSPECTION DEVICE

TECHNICAL FIELD

The present invention relates to an inspection device that detects a magnetic foreign object contained in an inspection object conveyed on a conveyance route.

BACKGROUND ART

Powder and granular materials, molded parts, various wrapped products, and the like have a risk of foreign object contaminating caused by coming off of a fixed object such as a screw in a manufacturing step, chipping of a blade in a cutting step, and the like. A high performance sensor is required for removal of a fine foreign object mixed in an inspection object in continuous mass conveyance of inspection objects.

Inspection methods such as optical inspection and fluoroscopic inspection using X-ray have been conventionally used. However, these methods cannot be employed in some modes of wrapping and conveyance and there is a demand for a method of detecting a foreign object in another principle.

As one of the methods of detecting a foreign object, there is a method of detecting remanent magnetization of a magnetic foreign object moving along a conveyance route with a magnetic sensor. However, it is known that detection of a magnetic foreign object of a fine size is difficult because a value of the remanent magnetization of such an object is extremely small.

The detection of a fine magnetic foreign object requires ingenuities such as numerical processing by a microcomputer or the like and removal of noise from a detection signal detected by the magnetic sensor through an arrangement of magnetic sensor elements and analog circuit processing.

For example, as a noise reduction technique, the following technique is known: multiple magnetic sensors having high directivity in a width direction of a conveyance route are arranged in the width direction of the conveyance route and correlations of detection signals of the multiple magnetic sensors are calculated to emphasize a detection signal of the magnetic foreign object and thereby reduce the noise level relative to the detection signal (refer to Patent Literature 1). This can improve the SN ratio of the detection signal buried in the noise.

As another noise reduction technique, the following technique is known: multiple magnetic sensor pairs each including an upper magnetic sensor and a lower magnetic sensor facing each other in the up-down direction with a conveyance route therebetween are arranged in a width direction of the conveyance route and differential calculation is performed on detection signals of the upper magnetic sensors and the lower magnetic sensors to reduce noise (refer to Patent Literature 2). This can improve the SN ratio of the detection signal buried in the noise.

CITATION LIST

Patent Literature

PTL 1: Japanese Patent No. 5695428
PTL 2: Japanese Patent No. 6121689

SUMMARY OF INVENTION

Technical Problem

In Patent Literature 1, a magnetic field detection direction of each magnetic sensor is the width direction of the conveyance route and the magnetic foreign object is magnetized in a direction perpendicular to a conveyance surface of the conveyance route. In such a configuration, there is formed a dead band in which magnetic detection sensitivity becomes zero in the case where the magnetic foreign object passes below the center of the magnetic sensor.

Moreover, since the magnetic field detection direction of each magnetic sensor is the width direction of the conveyance route, the polarity reverses at the center of the sensor and the positive or negative of the detection signal also reverses with respect to the width direction.

Formation of the dead band and unstable waveforms, that is reversal of positive or negative of the detection signal depending on the detection position make it difficult to improve the detection sensitivity in the signal processing.

Moreover, since the correlations of the detection signals of the magnetic sensors are calculated in the signal processing of Patent Literature 1, the technique of Patent Literature 1 requires timing signal generating unit and waveform comparison with finite template waveforms needs to be performed. However, in the case where the inspection objects are powder or granular objects or the like and are continuously conveyed, it is difficult to detect timing of cutting the continuously-detected signal into a unit of the template waveform and such a method is difficult to use in this case.

Moreover, in the case where the conveyed inspection objects are individually wrapped, the following problem may occur. If the inspection objects overlap one another, the start timing of one waveform template comes in the middle of the previous template waveform because the template waveforms are created in the units of individual wrapping, and the waveform comparison cannot be correctly performed.

In a conventional metal detection device described in Patent Literature 2, the signals of the paired magnetic sensors facing each other in the up-down direction are subjected to the differential calculation. In the case where the density of magnetic flux generated by disturbance noise in the upper magnetic sensor is not equal to that in the lower magnetic sensor, the noise cannot be sufficiently removed by the differential calculation and the detection accuracy of the magnetic foreign object thereby decreases.

Although Patent Literature 2 states that motors are arranged substantially in the middle of the pairs of the upper magnetic sensors and the lower magnetic sensors to equalize effects of motor noise, this requires fine position adjustment of the motors and the magnetic sensors and disturbance noise cannot be completely removed by the differential calculation. Thus, the detection accuracy of the magnetic foreign object decreases.

In order to improve removal rate of in-phase noise by the differential calculation, a method of adjusting the magnetic detection sensitivities of the upper magnetic sensor and the lower magnetic sensor to equalize the disturbance noise amount is conceivable. However, this requires work of adjustment.

The present invention has been made in view of the aforementioned problems and an object thereof is to provide an inspection device that can perform continuous inspection without a dead band and a change in a polarity of a detection signal waveform irrespective of a passing position of an inspection object. Moreover, another object is to provide an inspection device that can highly-accurately detect a fine magnetic foreign object in an inspection object without the need for adjustment of positions of noise sources and magnetic sensors and adjustment of magnetic detection sensitivities of the magnetic sensors.

Solution to Problem

In order to solve the aforementioned problems, one embodiment of the present invention is an inspection device characterized in that the inspection device comprises: a conveying unit configured to convey an inspection object along a conveyance route; a plurality of magnetic detectors configured to detect a magnetic field generated by remanent magnetization of a magnetic foreign object contained in the inspection object; and a computation unit configured to perform processing of multiplying detection signals of the plurality of magnetic detectors together and perform processing of multiplying the detection signals for the same inspection object conveyed by the conveying unit together.

Advantageous Effects of Invention

The present invention enables continuous inspection without a dead band and a change in a polarity of a detection signal waveform irrespective of a passing position of an inspection object. Moreover, the present invention enables highly accurate detection of a fine magnetic foreign object in an inspection object without the need for adjustment of positions of noise sources and magnetic sensors and adjustment of magnetic detection sensitivities of the magnetic sensors.

DESCRIPTION OF EMBODIMENTS

Embodiments of the present invention are described below in detail.

First Embodiment

Figure 1:
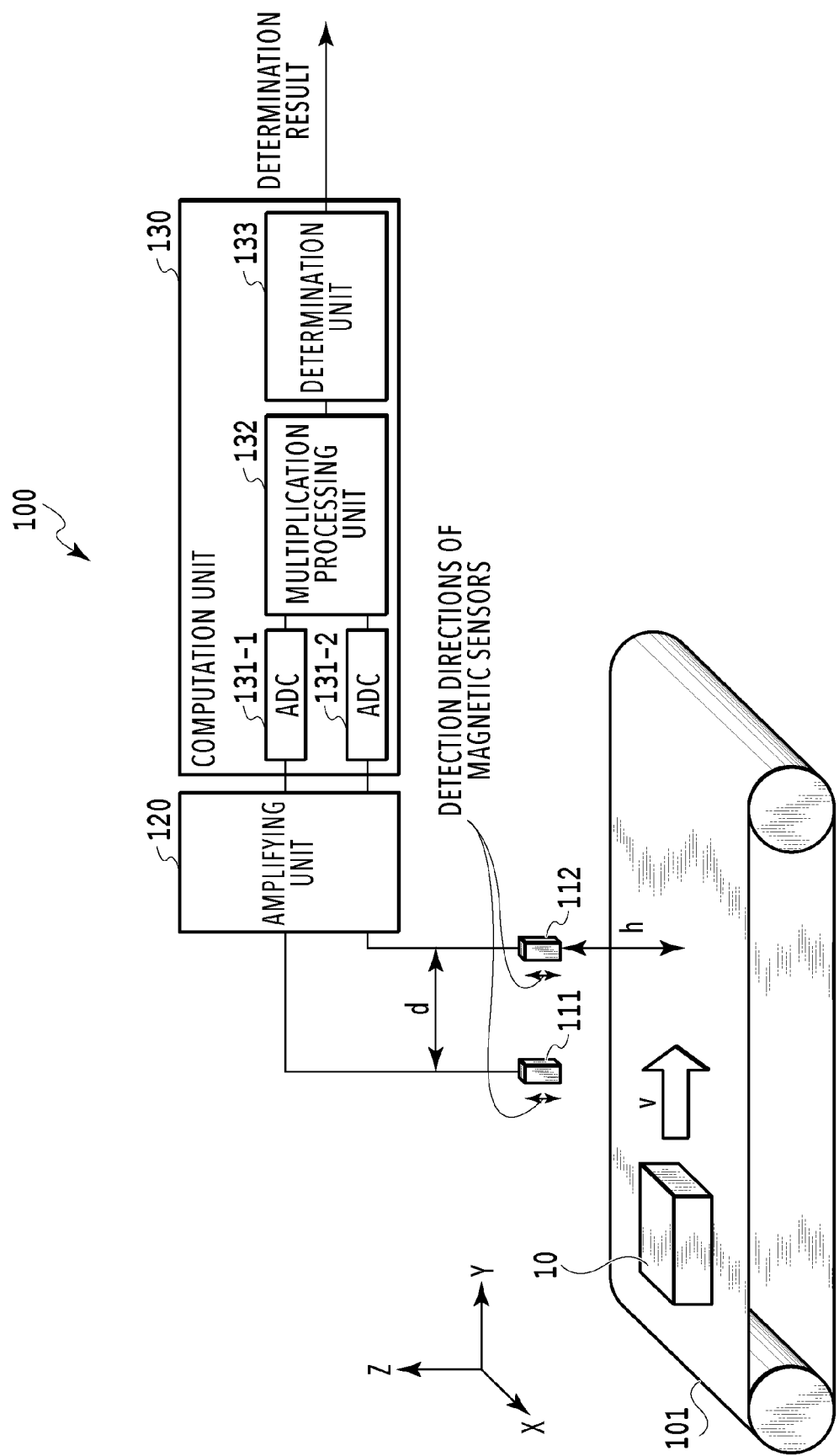
FIG. 1 is a schematic configuration diagram of an inspection device according to a first embodiment of the present invention.

FIG. 1 illustrates a configuration of an inspection device according to a first embodiment of the present invention. The inspection device 100 includes a conveyance route 101 that conveys an inspection object 10 at a moving speed v, a first magnetic detector 111 and a second magnetic detector 112 that detect magnetism of a magnetic foreign object near or inside the inspection object 10, an amplifying unit 120 that amplifies detection signals of the first magnetic detector 111 and the second magnetic detector 112, and a computation processing unit 130 that performs processing of multiplying the detection signal of the second magnetic detector 112 by a signal obtained by delaying the detection signal of the first magnetic detector 111.

In the configuration illustrated in FIG. 1, in order to simply the description, it is assumed that each of the first magnetic detector 111 and the second magnetic detector 112 has one magnetic sensor and the magnetic sensors form a pair. One magnetic sensor MS1 is arranged at a position at a height h from a conveyance surface as the first magnetic detector 111 whose magnetic field detection direction coincide with a direction perpendicular to the conveyance surface and one magnetic sensor MS2 is arranged at an interval of distance d from the magnetic sensor MS1 toward the exit side (downstream side) in the conveyance direction as the second magnetic detector 112.

The two magnetic sensors MS1, MS2 desirably have as similar characteristics as possible and at least desirably have such characteristics that, even if the heights of detection waveforms are different, periods from start to end of fluctuation of the waveforms are substantially the same. Note that the distance d between the two magnetic sensors MS1, MS2 is a distance between detections positions of the respective sensors. The positions of the two magnetic sensors MS1, MS2 in a width direction orthogonal to the conveyance direction of the conveyance route 101 do not have to be the same but are preferably the same from the viewpoint of computation processing to be described later.

The conveyance route 101 may be, for example, conveying unit for linearly conveying the inspection object such as a conveyor belt. The inspection object 10 may be a powder or granular object, a small piece, or in a form individually wrapped in a packaging material such as a bag or a box. Note that the packaging material is made of a non-magnetic material. The magnetic foreign object is contained inside or near the inspection object, is assumed to be a piece of rust, a screw, a fragment of a blade, or the like, and contains a magnetic material.

The magnetic sensors of the first magnetic detector 111 and the second magnetic detector 112 are arranged such that the magnetic field detection directions of the magnetic sensors are perpendicular to the conveyance surface. Accordingly, the polarities of the detection signal waveforms of the first magnetic detector 111 and the second magnetic detector 112 are constant irrespective of the passing position of the magnetic foreign object. If the polarities of the detection signal waveforms are constant, the computation processing can be simplified in the case where multiple magnetic sensors are aligned in the width direction of the conveyance route.

Figure 2:
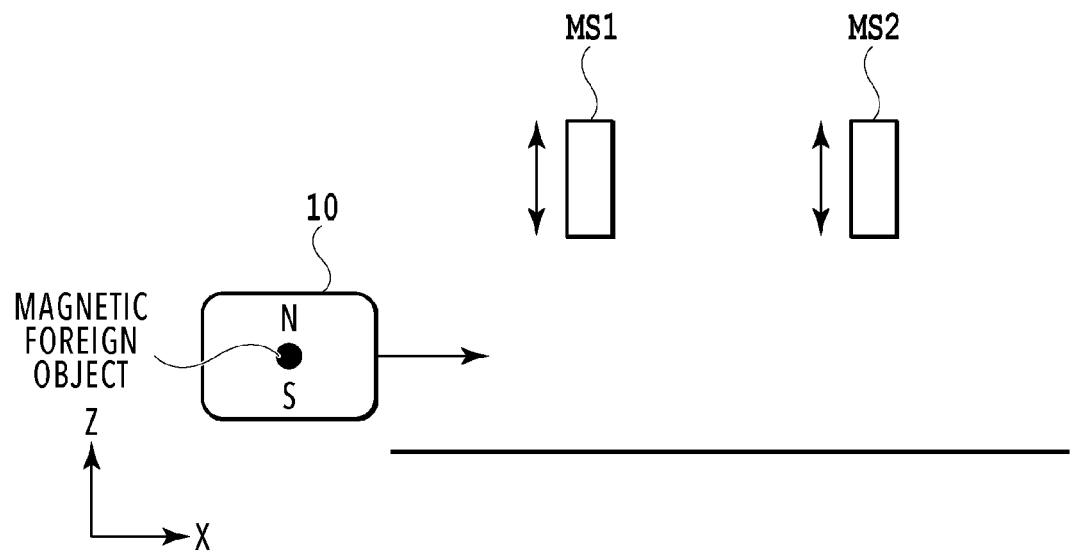
FIG. 2 illustrates magnetic sensors and a graph of detection signals.
Figure 2:
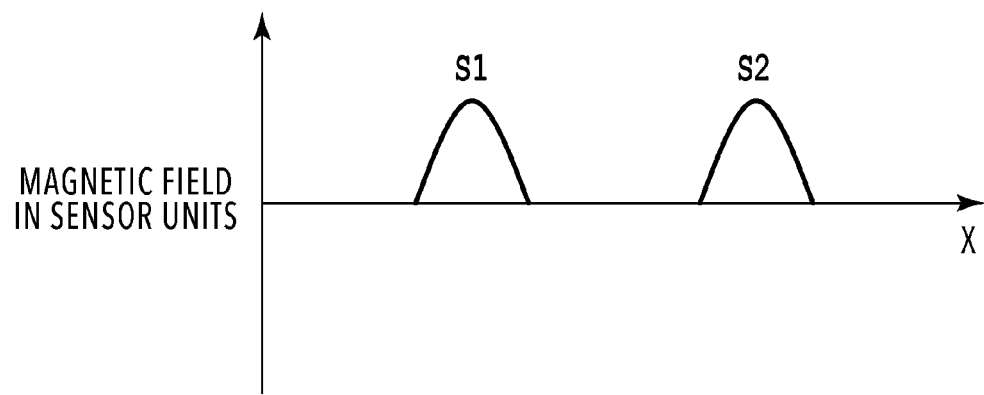

Part (a) of FIG. 2 illustrates the case where magnetic field detection directions of two magnetic sensors arranged away from each other in the width direction of the conveyance route are perpendicular to the conveyance surface and part (b) of FIG. 2 illustrates magnetic field waveforms detected by the magnetic sensors in this case. Meanwhile, part (a) of FIG. 3 illustrates the case where magnetic field detection directions of two magnetic sensors arranged away from each other in the width direction of the conveyance route are parallel to the conveyance surface and part (b) of FIG. 3 illustrates magnetic field waveforms detected by the magnetic sensors in this case.

Figure 3:
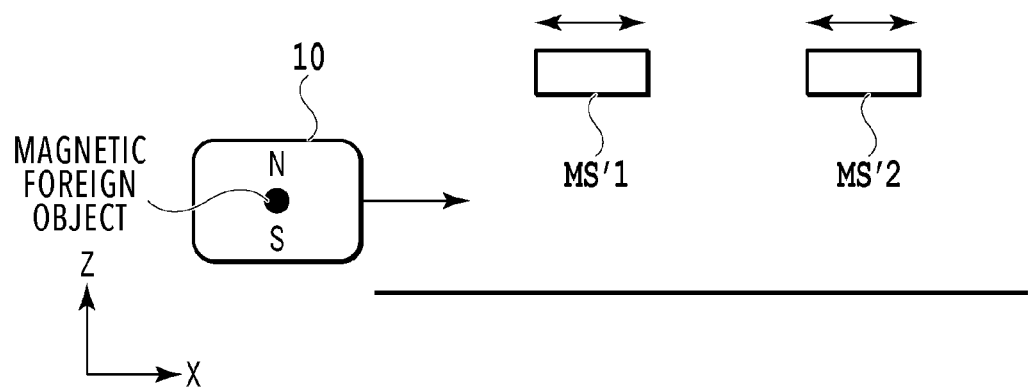
FIG. 3 illustrates magnetic sensors and a graph of detection signals.
Figure 3:
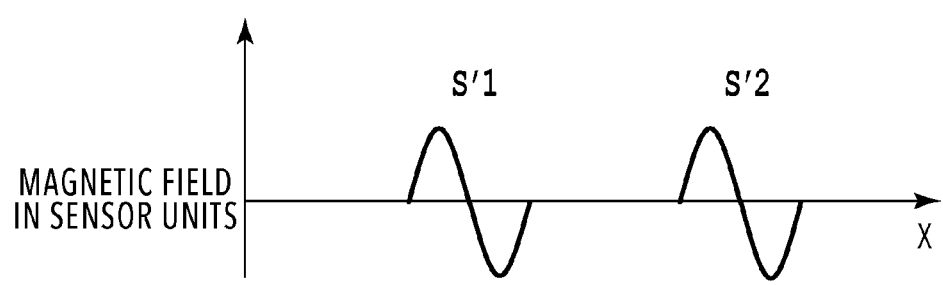

As illustrated in part (a) of FIG. 3, in the case where each magnetic sensor is arranged such that the magnetic field detection direction thereof coincides with the width direction of the conveyance route and a magnetic body with a magnetic polarity extending in the direction perpendicular to the conveyance surface is moved, as illustrated in part (b) of FIG. 3, the magnetic field in the magnetic field detection direction is zero in a situation where the position of the magnetic body in an x direction that is the width direction is at the center of the magnetic sensor and the polarity of the detection waveform vary at both ends. Accordingly, the detection waveform is unstable.

Meanwhile, as illustrated in part (b) of FIG. 2, in the embodiment, since the magnetic sensors are arranged in the width direction such that the magnetic field detection directions thereof are perpendicular to the conveyance surface, the magnetic field of each magnetic sensor does not reverse with respect to the position of the magnetic body in the x direction that is the width direction and a stable waveform varying in a given direction is obtained. The perpendicularity of each magnetic sensor to the conveyance surface needs to be set such that the turning of the phase and the reversal of the polarity are avoided. Note that, although part (a) of FIG. 2 illustrates the configuration in which the waveform of the magnetic field detected by each magnetic sensor fluctuates in a positive direction in the case where the magnetic polarity of the magnetic foreign object is perpendicular to the conveyance surface, also in the configuration in which the waveform of the detected magnetic field fluctuates in a negative direction, the magnetic field detection direction needs to be similarity aligned such that the polarities of the detection waveforms of the magnetic fields are aligned.

Figure 4:
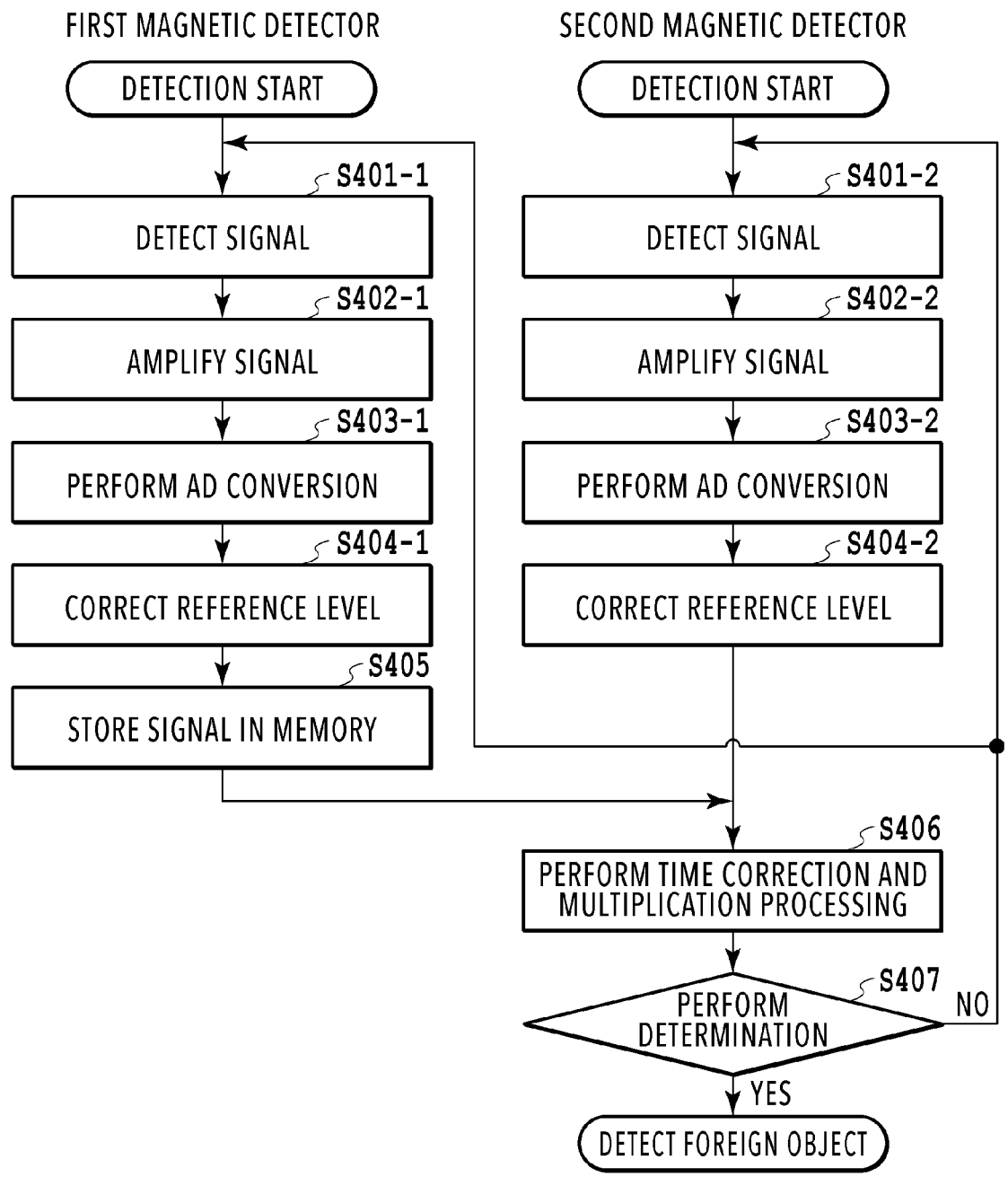
FIG. 4 is a flowchart illustrating processing of detecting a magnetic foreign object in the inspection device according to the first embodiment of the present invention.
Figure 5:
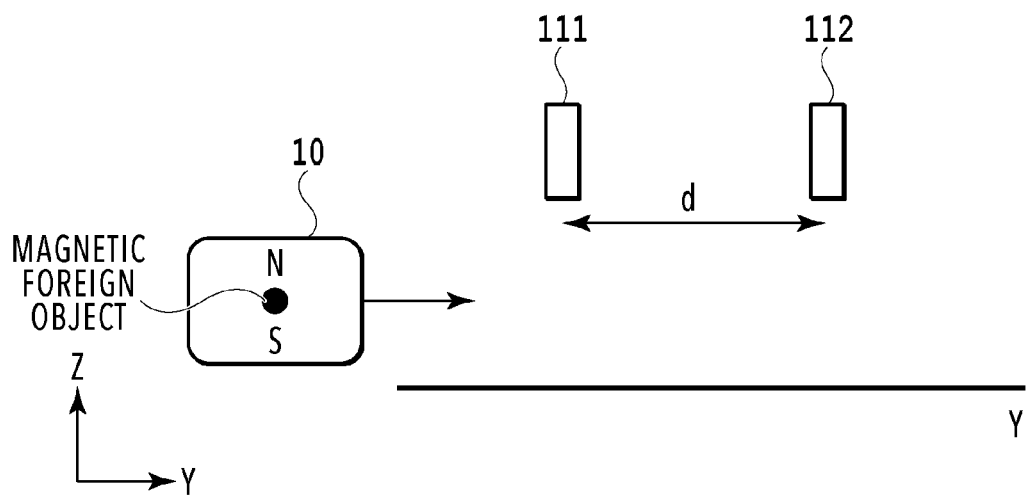
FIG. 5 illustrates magnetic sensors and graphs of detection signals.
Figure 5:
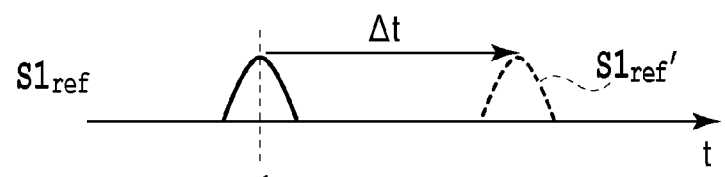
Figure 5:
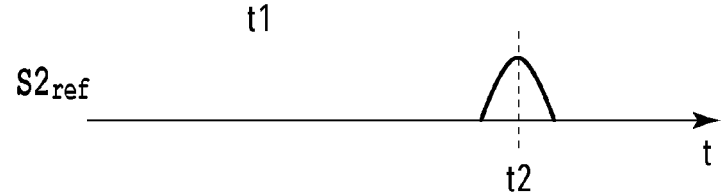
Figure 5:
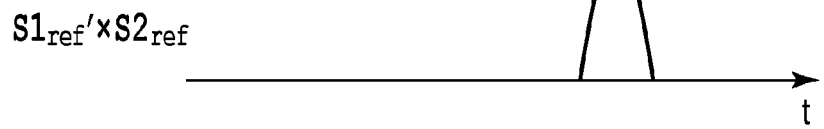
Figure 6:
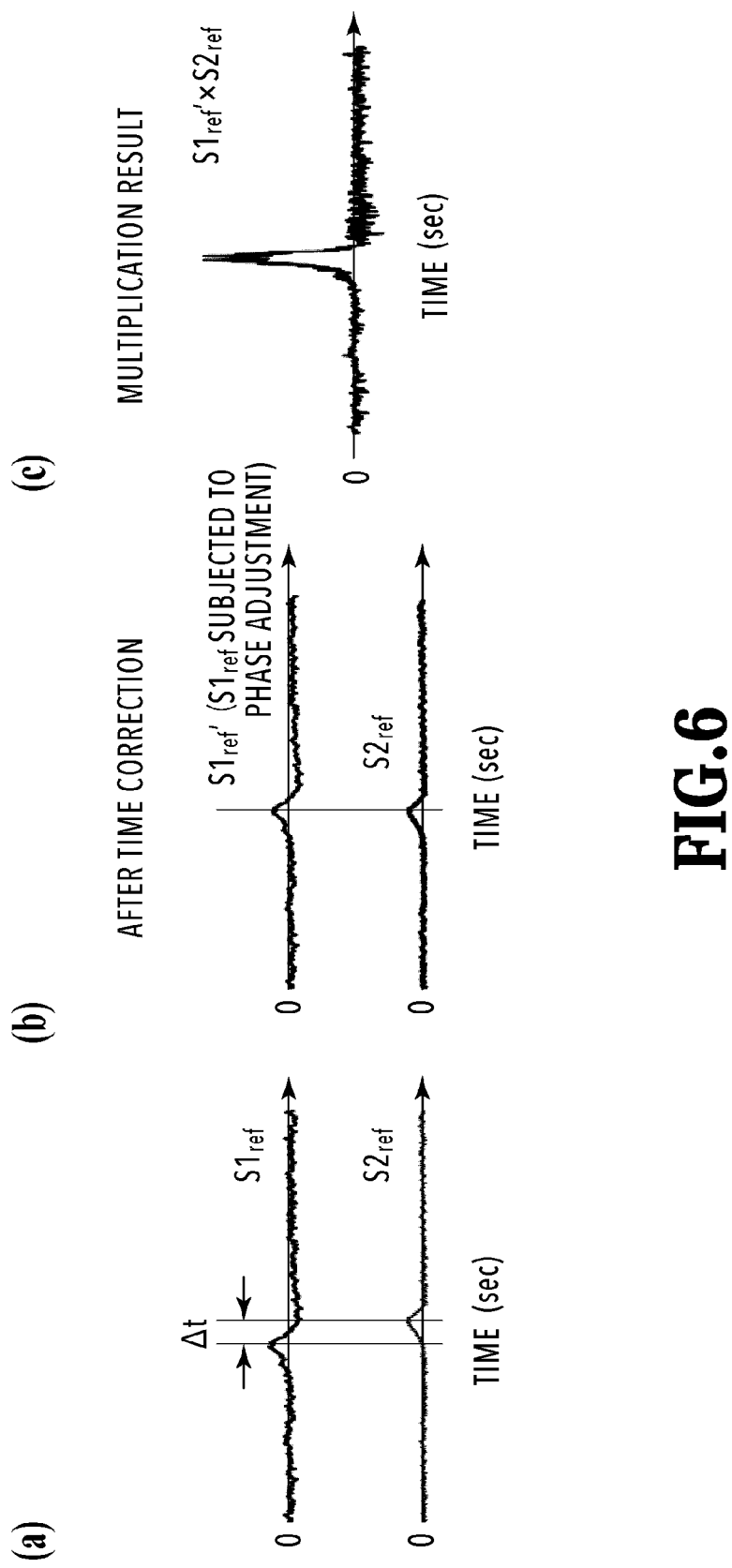
FIG. 6 includes graphs of two detection signals and a multiplication result of the detection signals.

FIG. 4 illustrates a flowchart explaining a method of processing the detection signals in the inspection device according to the first embodiment of the present invention. As described by using FIGS. 5 and 6, FIG. 5 illustrates a conceptual view of the arrangement and the detection waveforms of the first magnetic detector 111 and the second magnetic detector 112 and FIG. 6 includes schematic diagrams of actually-measured detection waveforms. First, the signals outputted from the magnetic sensor MS1 of the first magnetic detector 111 and the magnetic sensor MS2 of the second magnetic detector 112 are detected (S401-1, S401-2).

Next, the detection signals of the magnetic sensors MS1, MS2 are amplified in the amplifying unit 120 (S402-1, S402-2) and are digitized (subjected to AD conversion) to digital values in AD convertors 131-1, 131-2 in the computation processing unit 130 (S403-1, S403-2). This amplification may be DC amplification. However, performing AC amplification enables removal of a DC magnetic field component of geomagnetism and the like. Moreover, a DC component may be removed after the AD conversion or removed in the circuit before the AD conversion.

Next, in a multiplication processing unit 132, level correction is performed on each of the detection signal S1 of the first magnetic detector 111 and the detection signal S2 of the second magnetic detector 112 subjected to the AD conversion, according to corresponding one of the following formulae (S404-1, S404-2). The level correction is performing numerical value correction on reference levels such that the detection signal S1 fluctuates around zero, and can be performed by subtracting an average value of the detection signal in a period where there is no inspection object ($t'1 \leq t' \leq t'2$) from the detection signal but may be performed by using another method.

$$S1_{ref}(t) = S1(t) - \frac{\int_{t'1}^{t'2} S1(t')dt'}{t'2 - t'1} \quad \text{(Formula 1)}$$

$$S2_{ref}(t) = S2(t) - \frac{\int_{t'1}^{t'2} S2(t')dt'}{t'2 - t'1} \quad \text{(Formula 2)}$$

Next, at least one of the detection signals is stored in a memory in the multiplication processing unit 132 (S405) and time correction of Δt is performed on at least one of the detection signals, in the embodiment, on the detection signal S1 of the first magnetic detector 111 such that timings at which the magnetic foreign object passes the respective magnetic detectors or timings at which the inspection object 10 comes closest to the respective magnetic detectors match each other in the detection waveforms of the first magnetic detector 111 and the second magnetic detector 112, that is the detection waveforms corresponding to the magnetic foreign object have the same phase (S406). In the case where a magnetic body such as iron having a magnetization direction coinciding with a direction perpendicular to the conveyance surface is conveyed at the speed v on the conveyance surface, similar detection waveforms are obtained with a time difference Δt as in detection signals $S1_{ref}$, $S2_{ref}$ illustrated in parts (b) and (c) of FIG. 5 and parts (a) and (b) of FIG. 6. Δt is a value obtained by dividing the distance d between the magnetic sensors forming a pair by the conveyance speed v as described in the following formula.

$$\Delta t = d/v \quad \text{(Formula 3)}$$

Next, in the multiplication processing unit 132, the detection signal $S2_{ref}$ of the second magnetic detector 112 is multiplied by the detection signal $S1_{ref}'$ of the first magnetic detector subjected to the time correction (S406) to obtain a multiplication waveform S12.

$$S12(t) = S1_{ref}(t - \Delta t) \times S2_{ref}(t) \quad \text{(Formula 4)}$$
$$= S1_{ref}'(t) \times S2_{ref}(t)$$

As illustrated in part (d) of FIG. 5 and part (c) of FIG. 6, the multiplication waveform S12 takes a positive value in the case where the detection signals $S1_{ref}'$, $S2_{ref}$ have values indicating magnetic fields with the same polarity and takes a negative value in the case where the detection signals $S1_{ref}'$, $S2_{ref}$ have values indicating magnetic fields with different polarities. Particularly, noise components are present near zero as a result of the level correction and have waveforms in which the polarities randomly change at short periods. Thus, the polarities of the noise components in the detection signals $S1_{ref}'$, $S2_{ref}$ rarely match each other. Accordingly, the noise components in the detection signals $S1_{ref}'$, $S2_{ref}$ are substantially in a reverse phase relationship and the result of the multiplication of these signals thus takes a negative value. Accordingly, a determination unit 133 can detect the magnetic foreign object by determining that the magnetic foreign object is present in the case where the multiplication waveform S12 is a predetermined positive value or more in (S407). Note that, in the case where the multiplication waveform S12 is less than the predetermined positive value, the processing returns to S401-1, S401-2.

A large difference in the peak value between the signal component detecting the magnetic foreign object and the signal component detecting only the noise can be achieved in the multiplication waveform S12 subjected to the multiplication processing by performing the aforementioned computation and the SN ratio is clearly improved.

Figure 7:
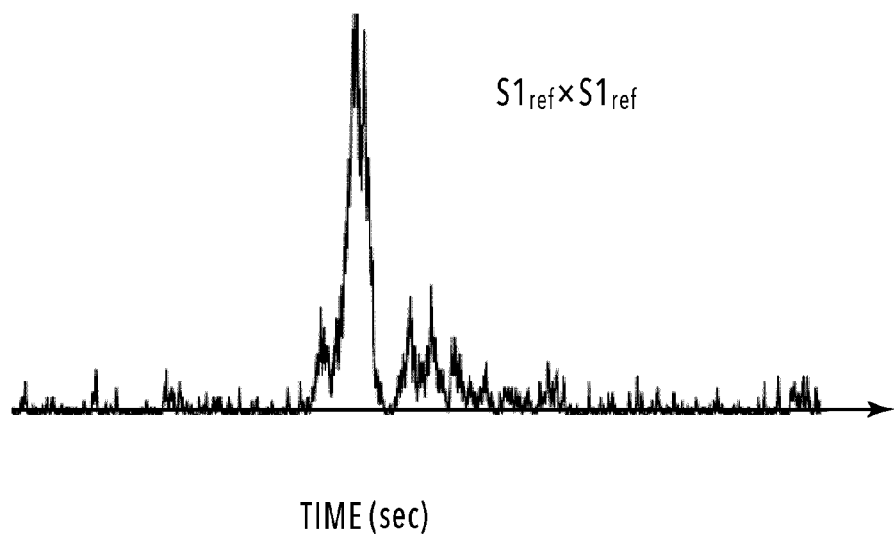
FIG. 7 is a graph of a multiplication result of two detection signals.

FIG. 7 illustrates a result of the multiplication processing in the case where the detection signal $S2_{ref}$ of the second magnetic detector 112 is assumed to be exactly the same as the detection signal $S1_{ref}$ of the first magnetic detector 111, that is a result of processing of multiplying the detection signal $S1_{ref}$ by itself. In this case, since the noise components have the same phase, the multiplication result takes a positive value as in the peak formed by detection of the magnetic foreign object. However, in actual, the case where all noise components have the same phases as those in the other detection signal as in FIG. 7 in which the same detection signals are multiplied rarely occurs and most of the noise components have opposite phases to those in the other detection signals and most of the multiplication result of the noise components takes a negative value as in FIG. 6.

The characteristics of the embodiment are such that the phase of the signal obtained by detecting the magnetic foreign object and the phase of the detection signal due to the noise components are separated by detecting the inspection object 10 at two positions in the conveyance direction and multiplying the detection signal by the detection signal subjected to the level correction and the time correction to emphasize a remanent magnetization component of the magnetic foreign object in the detection signal and suppress the noise components. Moreover, since the signals of the first magnetic detector 111 and the second magnetic detector 112 can be sequentially calculated and a template waveform or the like for comparison does not have to be prepared in advance, the inspection objects 10 do not have to be passed through the inspection device 100 while being separated from one another in units of template waveform and it is possible to continuously inspect the inspection objects without interruption and to inspect multiple inspection objects overlapping one another.

Description is given of the case where the detection waveforms of the first magnetic detector 111 and the second magnetic detector 112 are waveforms fluctuating on the positive side. However, since the multiplication result in the detection of the magnetic foreign object is positive also in the case where the detection waveforms of the first magnetic detector 111 and the second magnetic detector 112 are waveforms fluctuating on the negative side, only a threshold on the positive side needs to be considered. The inspection device 100 determines that the inspection object containing the magnetic foreign object has passed in the case where the multiplication result exceeds a predetermined threshold. In the case where the inspection device 100 detects the magnetic foreign object, it is preferable to take measures such as removing the inspection object containing the magnetic foreign object from the conveyance route. Moreover, the inspection device 100 includes an alarm unit and gives an alarm while performing control of stopping the conveyance on the conveyance route. Furthermore, in the case where the magnetism sensing direction of one of the first magnetic detector 111 and the second magnetic detector 112 is set to be opposite to that of the other, the multiplication result in the detection of the magnetic foreign object is negative and the multiplication result of the noise components is positive. Accordingly, it is only necessary to set a threshold on the negative side.

Figure 8:
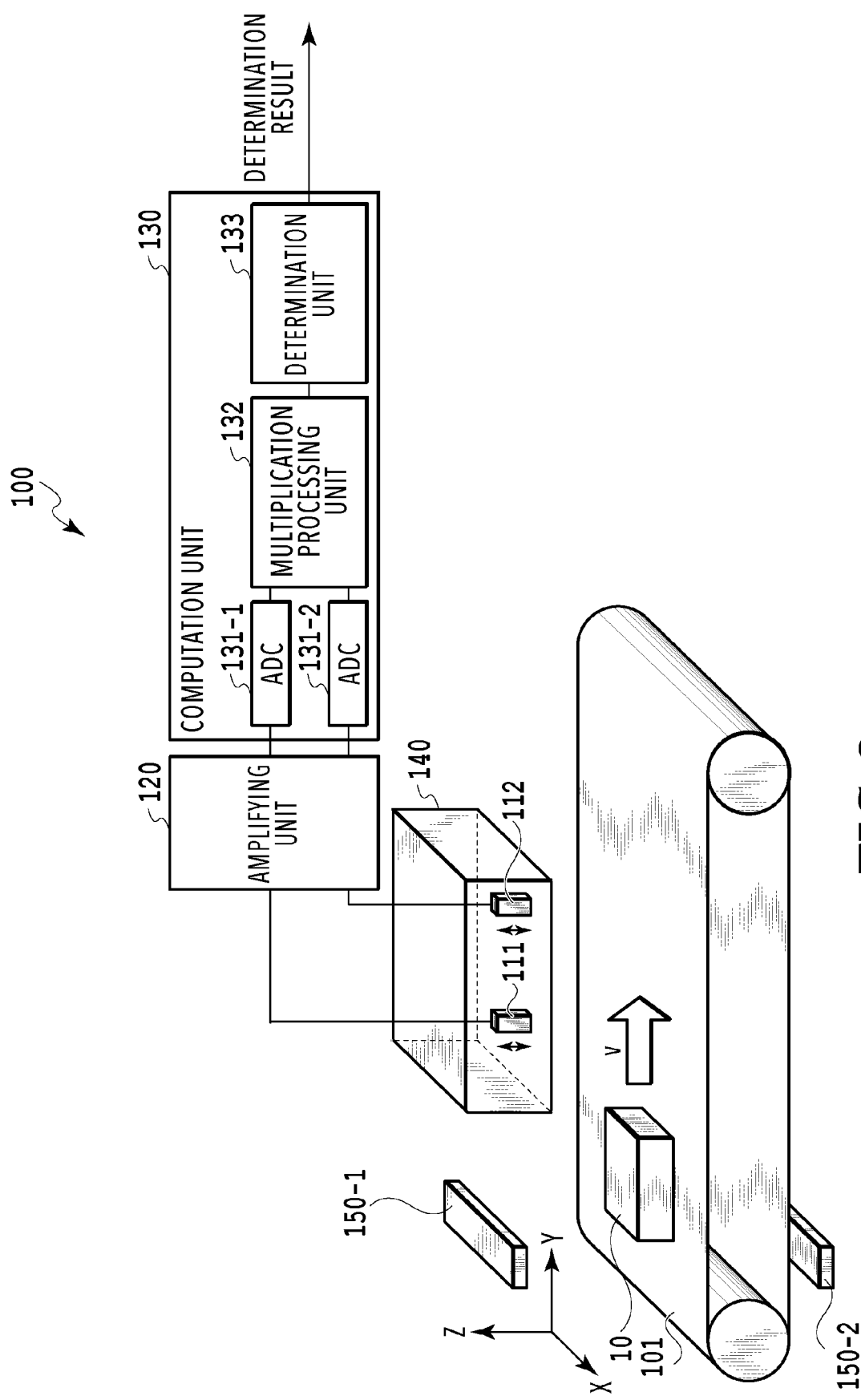
FIG. 8 is a schematic configuration diagram illustrating another mode of the inspection device according to the first embodiment of the present invention.

Moreover, as illustrated in FIG. 8, the inspection device 100 may further include magnetic shielding unit 140 and unit 150 for magnetizing the magnetic foreign object. The magnetizing unit 150 is preferably formed of upper magnetizing unit 150-1 located above the inspection object and lower magnetizing unit 150-2 located below the inspection object but may be provided only above or below the inspection object.

The inspection device 100 may include the magnetic shielding unit 140 made of a high magnetic permeability material to shield effects of an external magnetic field. The magnetic shielding unit 140 is configured such that a surface facing the conveyance route 101 is open and the other five surfaces are made of the high magnetic permeability material to cover the first magnetic detector 111 and the second magnetic detector 112. Providing the magnetic shielding unit 140 can reduce the effects of exterior noise entering the first magnetic detector 111 and the second magnetic detector 112 and improve the S/N ratio. The high magnetic permeability material may be permalloy, silicon steel plate, or the like.

In order to detect a fine magnetic foreign object, the inspection device 100 preferably further includes the magnetizing unit 150. The magnetizing unit 150 is arranged closer to the entrance of the conveyance route 101 than the position of the first magnetic detector 111 is. The magnetizing unit 150 is formed of members such as magnets fixed above and below the conveyance route 101 such that the inspection object 10 can pass. A direction in which the magnetic foreign object is magnetized may be any direction. However, if the magnetizing direction is set to a direction perpendicular to the conveyance surface of the conveyance route 101, the magnetizing direction coincides with the magnetic detection directions of the first magnetic detector 111 and the second magnetic detector 112 and more accurate detection can be thus performed. Note that, in the case where the remanent magnetization of the magnetic foreign object is sufficiently large, the magnetizing unit 150 is unnecessary.

Moreover, although not illustrated in FIGS. 1 and 8, the inspection device 100 may include a display unit used to present the multiplication result of the detection signals as illustrated in part (c) of FIG. 6 to the user. The user can directly determine presence or absence of the magnetic foreign object from the multiplication result in addition to the determination by the determination unit 133.

Second Embodiment

Figure 9:
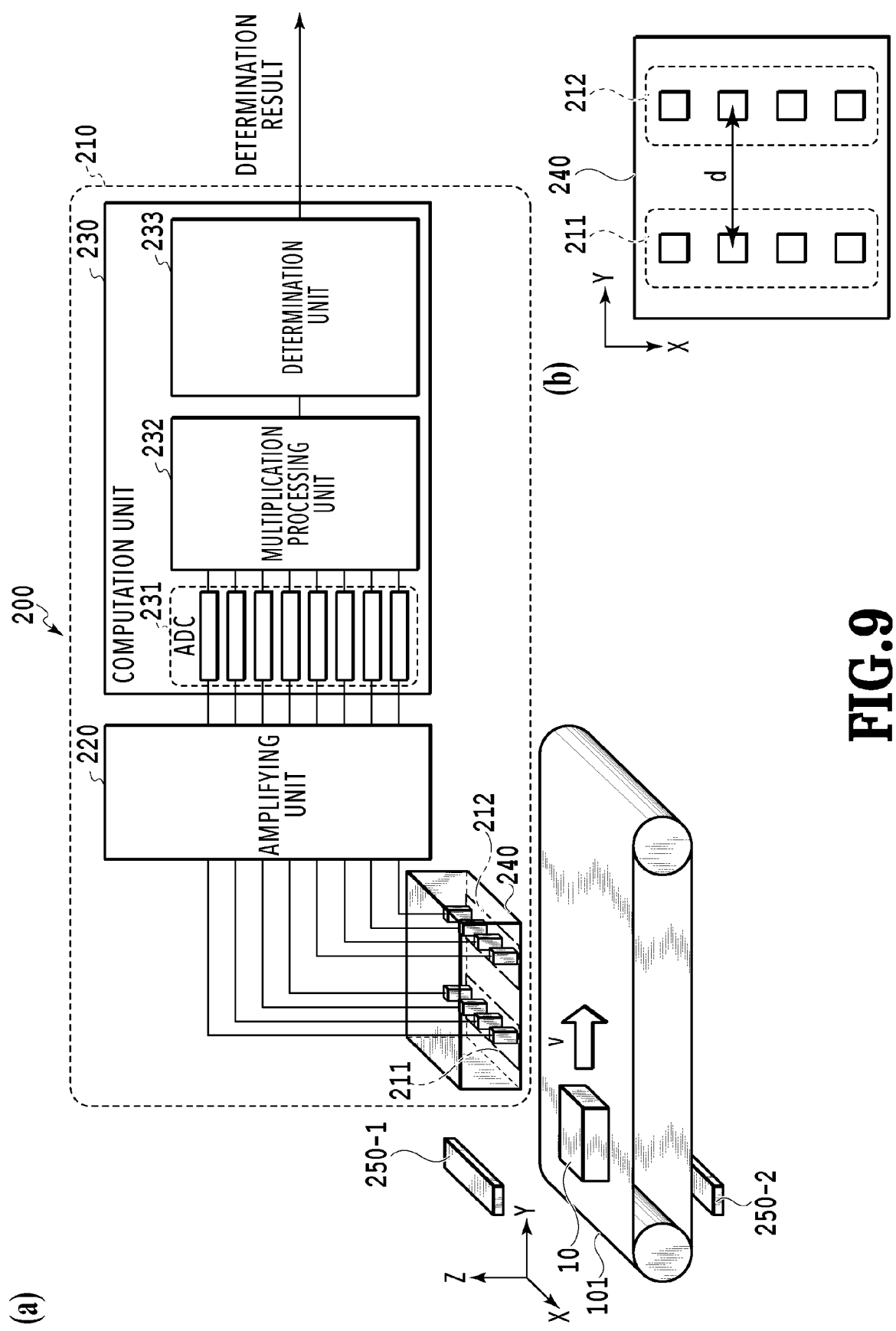
FIG. 9 is a schematic configuration diagram of an inspection device according to a second embodiment of the present invention.

FIG. 9 illustrates a configuration of an inspection device according to a second embodiment of the present invention. In the second embodiment, description is given of the configuration for improving the detection accuracy of the magnetic foreign object in the width direction of the conveyance route 101 and the perpendicular direction of the conveyance route 101. The inspection device 200 includes the conveyance route 101 that conveys the inspection object 10 at the moving speed v, a first magnetic detector 211 and a second magnetic detector 212 that detect magnetism of a magnetic foreign object near or inside the inspection object 10, an amplifying unit 220 that amplifies detection signals of the first magnetic detector 111 and the second magnetic detector 112, and a computation processing unit 230 that performs processing of multiplying the detection signal of the second magnetic detector 212 by a signal obtained by delaying the detection signal of the first magnetic detector 211.

In the first embodiment, description is given of the example in which each of the first magnetic detector 111 and the second magnetic detector 112 has one magnetic sensor. However, in this embodiment, each of the first magnetic detector 211 and the second magnetic detector 212 has multiple magnetic sensors in the width direction of the conveyance route 101. As many AD convertors 231 as the magnetic sensors are also provided depending on the number of magnetic sensors.

In this case, each of the magnetic sensors in the first magnetic detector 211 forms a pair with one of the magnetic sensors in the second magnetic detector 212 and detection signals of these paired magnetic sensors are processed as the detection signals S1, S2 in the computation processing unit 230. The paired magnetic sensors only need to be arranged away from each other with a predetermined distance d in the conveyance direction and the positions thereof in the width direction orthogonal to the conveyance direction of the conveyance route 101 do not have to match each other. However, the positions in the width direction preferably match each other because this improves a degree of matching of the signal waveforms between the paired magnetic sensors and improves the SN ratio of the multiplication waveform S12 obtained in the aforementioned computation processing.

The multiple magnetic sensors forming each of the first magnetic detector 211 and the second magnetic detector 212 may be arranged on a line sector extending at the shortest length in the width direction of the conveyance route 101 as illustrated in part (b) of FIG. 9. Moreover, as long as the distance between the magnetic sensors in the conveyance direction is constant among the pairs of magnetic sensors, the positions of the pairs of the magnetic sensors in the conveyance direction may vary such that the magnetic sensors are obliquely arranged in the width direction or arranged in an arc shape, a substantially S shape, or any other shape.

The multiplication processing can be performed on a signal obtained by adding up the signals of the magnetic sensors in the first magnetic detector 211 and a signal obtained by adding up the signals of the magnetic sensors in the second magnetic detector 212 or may be performed on the signals of each pair of the magnetic sensors arranged at the interval d in the conveyance direction.

In the case where the multiplication processing is performed on each pair of magnetic sensors aligned one in front of the other in the conveyance direction, the inspection device 100 can determine that the magnetic foreign object has passed near the pair of magnetic sensors for which the multiplication result has exceeded the threshold. Thus, the passing position of the magnetic foreign object in the width direction of the conveyance route 101 can be determined.

Figure 10:
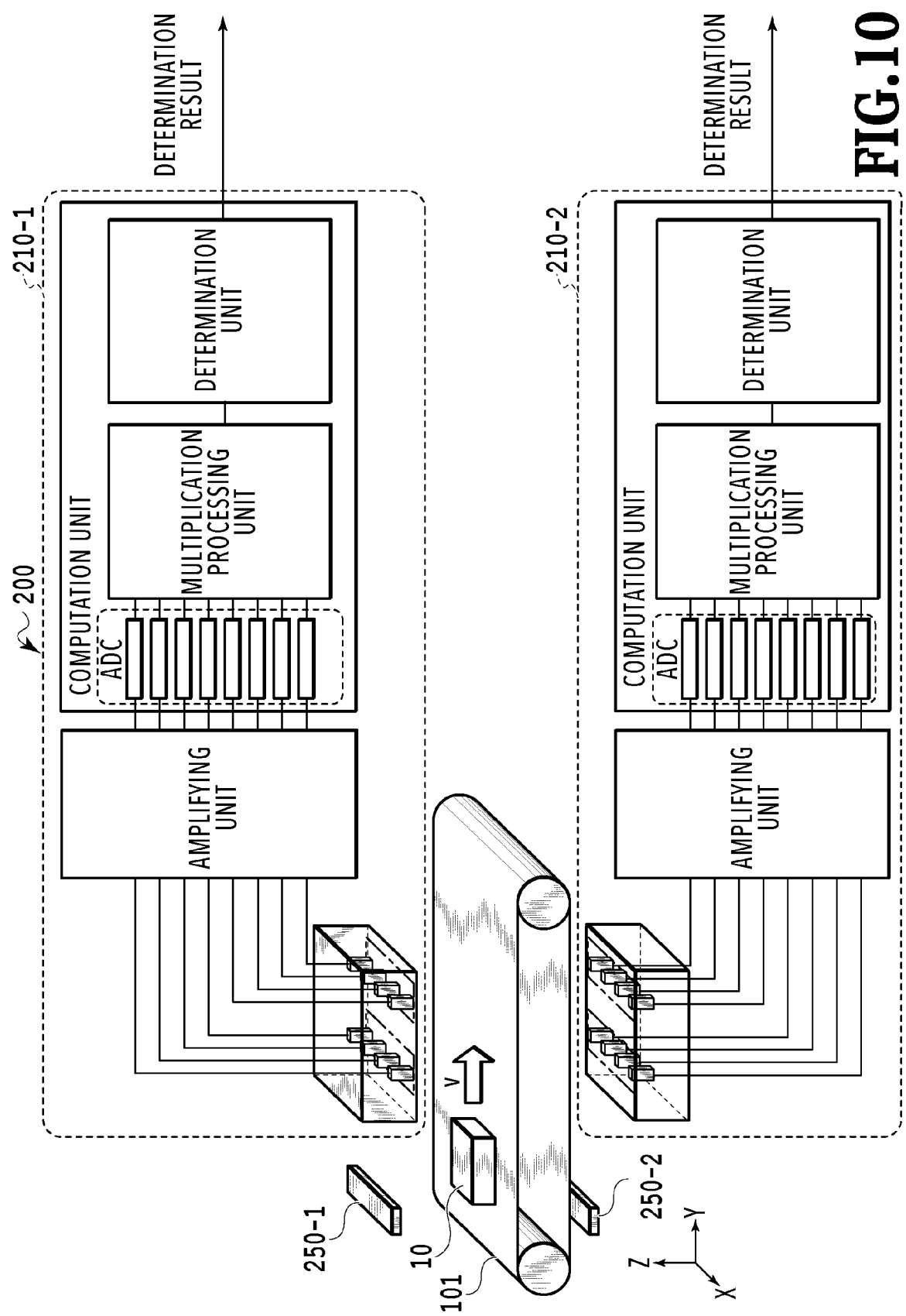
FIG. 10 is a schematic configuration diagram illustrating another mode of the inspection device according to the second embodiment of the present invention.

In order to improve the resolution in the height direction of the conveyance route 101, it is preferable to arrange a set of an upper magnetic detection unit 210-1 and a lower magnetic detection unit 210-2 above and below the conveyance route 101 such that the conveyance route 101 is arranged between the units as illustrated in FIG. 10. In order to prevent detection failure of the magnetic foreign object, the detectors may be arranged such that the center position of a space where the magnetic foreign object is assumed to pass in the direction perpendicular to the conveyance surface is at the middle of the upper magnetic detection unit 210-1 and the lower magnetic detection unit 210-2 and it is more preferable that the lower detection unit 210-2 is arranged below and near the conveyance surface. Specifically, the lower detection unit 210-2 is preferably arranged between a portion of a belt moving in the conveyance direction and a portion of the belt moving in the opposite direction to the conveyance direction in the looped belt forming the conveyance route 101, at a position directly below the portion of the belt moving in the conveying direction.

Third Embodiment

In a third embodiment, description is given of a configuration of an inspection device in the first embodiment and the second embodiment that is further improved in the detection accuracy of the magnetic foreign object. Note that description of matters that are the same as those in the first and second embodiments is omitted.

In the third embodiment, the computation processing unit 130, 230 in the inspection device 100, 200 further includes unit for performing averaging processing on the detection signals and periodic noise removing unit. The averaging processing can be performed on each of the detection signals of the first magnetic detector 111, 211 and the second magnetic detector 112, 212 by using these unit. The averaging processing may be moving average, arithmetic mean, or the like. The averaging processing can round the noise and improve the S/N ratio in the multiplication processing. Note that the averaging processing may be performed on the multiplication result.

Since the conveyance route 101 of the inspection device 100, 200 includes a motor, a power supply unit, and the like for operating the conveyor belt and the like, the first magnetic detector 111, 211 and the second magnetic detector 112, 212 are affected by periodic magnetic noise with a frequency of 50 Hz or 60 Hz and magnetic noise with a certain frequency component generated by a drive unit and the like.

Providing the magnetic shielding unit made of high magnetic permeability material around the first magnetic detector 111, 211 and the second magnetic detector 112, 212 as described above can reduce effects of noise. However, in order to detect a finer magnetic foreign object, effects of magnetic noise that cannot be completely removed by the magnetic shielding unit need to be reduced.

The magnetic noise with a certain frequency can be reduced by setting the magnetic sensor interval d between the first magnetic detector 111, 211 and the second magnetic detector 112, 212 as described in the formula 5.

$$d = (2n+1) \times \left(\frac{Tex}{2}\right) \times vex \quad \text{(Formula 5)}$$

In this formula, Tex is one period of the noise and vex is the conveyance speed in the conveyance route. As in the formula 5, setting the interval d between the magnetic sensors in the first magnetic detector 111, 211 and the second magnetic detector 112, 212 to a value obtained by multiplying an odd-number times a half period of a noise signal by the conveyance speed in the conveyance route causes noise components detected by the first magnetic detector 111, 211 and the second magnetic detector 112, 212 to be in a reverse phase relationship. Accordingly, in the case where the multiplication processing is performed, the multiplication results of the noise components take negative values and the effects of noise removal can be improved.

Note that although the formula 5 unit that the noise signal in the first magnetic detector 111, 211 is made to have exactly the opposite phase to the noise signal in the second magnetic detector 112, 212 by setting the magnetic sensor interval d and the conveyance speed vex such that d/vex is equal to an odd-number times the half period (Tex/2) of the noise signal, the present invention is not necessarily limited to this mode. For example, the multiplication result of the noise component can be preferably made to take a negative value also in the case of 0.8×Tex/2≤d/vex≤1.2×Tex/2. In this case, the value of the multiplication result also of a noise component that do not take a negative value can be made relatively small and the removal of the noise component is facilitated.

Moreover, in the case where the frequency component of the external noise is higher than the frequency component of the detection signal of the magnetic foreign object and in similar cases, the effects of the noise can be reduced based on the formula 4 by further adjusting the correction time. As described above, in the multiplication processing of the formula 4, the multiplication result takes a positive value in the case where the detection signals of the first magnetic detector 111, 211 and the second magnetic detector 112, 212 fluctuate in the same phase and takes a negative value in the case where the detection signals fluctuate in the opposite phases and a multiplication result of a negative value can be thereby determined as noise. Accordingly, if certain time correction is performed on periodic noise such that the reverse phase relationship is established between the noise signal of the first magnetic detector 111, 211 and the noise signal of the second magnetic detector 112, 212, the noise components subjected to the multiplication processing have the negative polarity and the effect of noise removable can be greatly improved. In other words, it is only necessary to add a correction value a to Δt for periodic noise removal as illustrated in the formula 6.

$$S12'(t) = S1_{ref}(t-(\Delta t+\alpha)) \times S2_{ref}(t) \quad \text{(Formula 6)}$$

Figure 11:
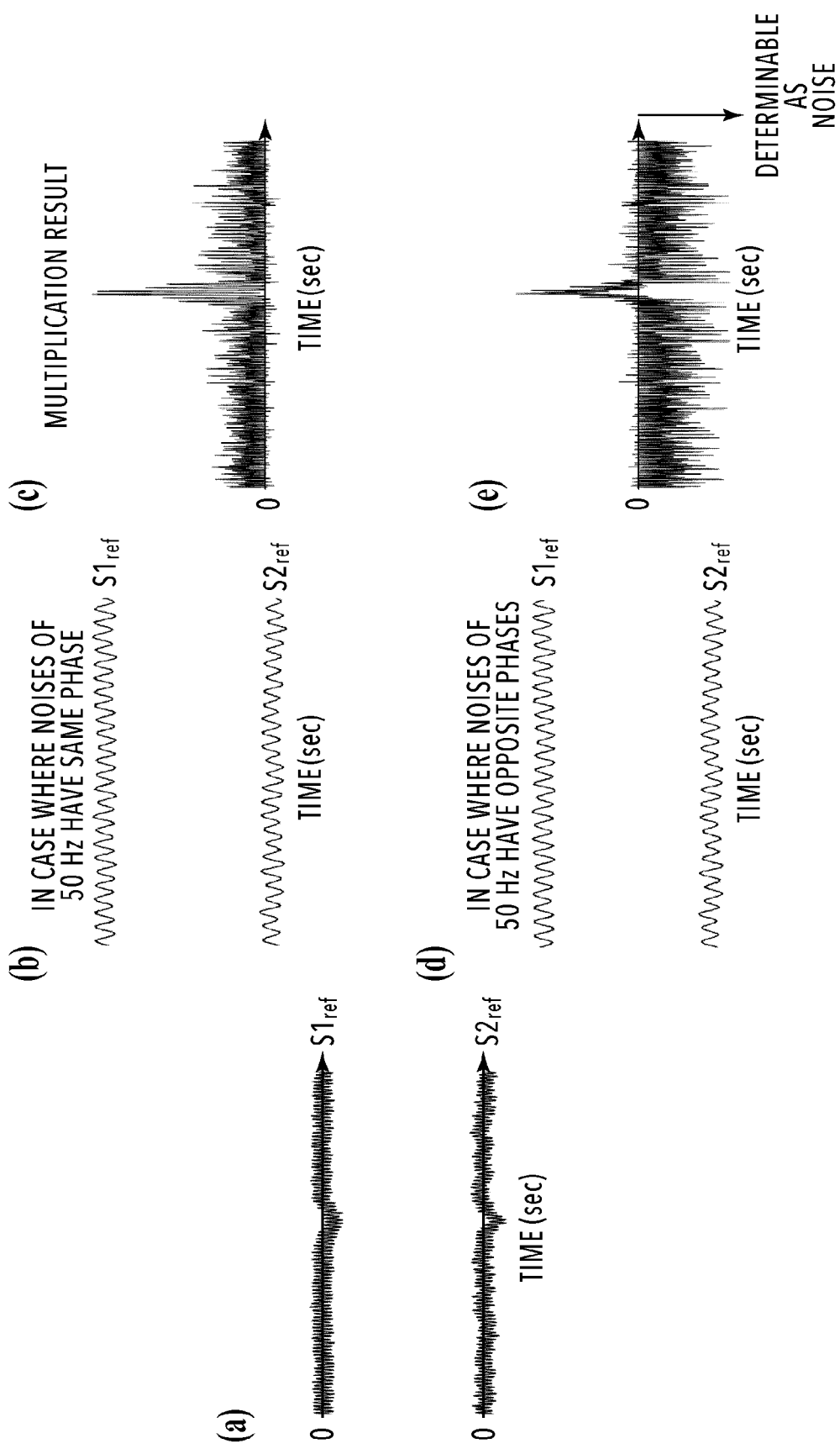
FIG. 11 includes graphs of two detection signals and multiplication results of the two detection signals.

Part (a) of FIG. 11 illustrates signal waveforms of the detection signal $S1_{ref}$ of the magnetic sensor in the first magnetic detector 111, 211 and the detection signal $S2_{ref}$ of the magnetic sensor in the second magnetic detector 112, 212 forming a pair with the magnetic sensor in the first magnetic detector 111, 211. Moreover, parts (b) and (c) of FIG. 11 illustrate results obtained in the case where the signal waveforms $S1_{ref}$, $S2_{ref}$ are adjusted such that the noise components of 50 Hz have the same phase and the adjusted signal waveforms $S1_{ref}$, $S2_{ref}$ are multiplied. Parts (d) and (e) of FIG. 11 illustrate results obtained in the case where the signal waveforms $S1_{ref}$, $S2_{ref}$ are adjusted such that the noise components of 50 Hz have the opposite phases and the adjusted signal waveforms $S1_{ref}$, $S2_{ref}$ are multiplied. As illustrated in parts (d) and (e) of FIG. 11, adjusting the noise components such that the noise components have the opposite phases greatly improves the S/N ratio.

The recognition of the periodical noise and the determination of correction value a for removal of the periodical noise can be performed in the computation processing unit after the detection signals of the magnetic detectors are subjected to the AD conversion.

Fourth Embodiment

Figure 12:
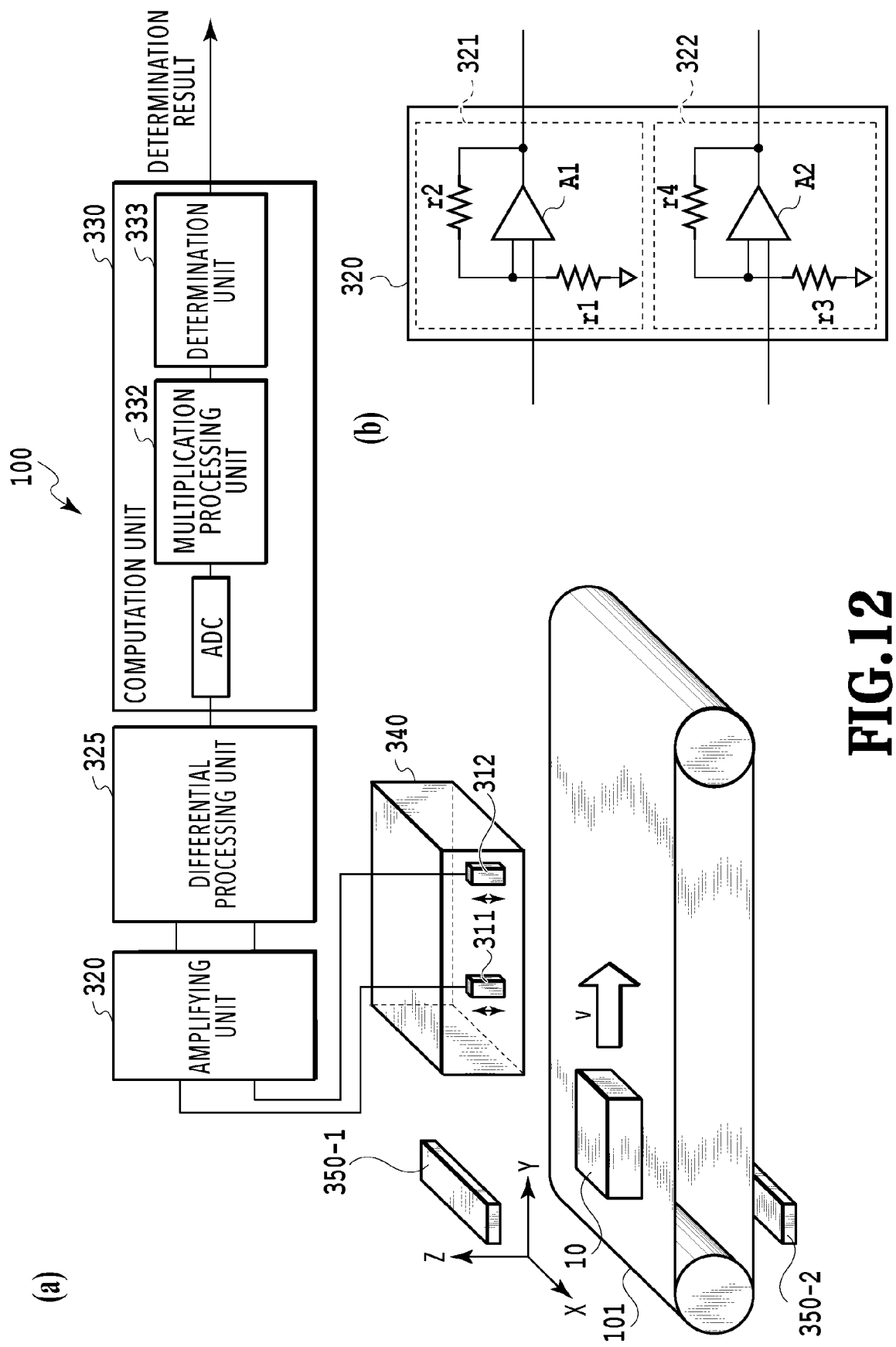
FIG. 12 is a schematic configuration diagram of an inspection device according to a fourth embodiment of the present invention.

Part (a) of FIG. 12 illustrates a configuration of an inspection device according to a fourth embodiment of the present invention. In the inspection device 300, a differential processing unit 325 is arranged upstream of a computation unit 330 and performs differential processing on detection signals from paired first magnetic detector 311 and second magnetic detector 312 whose detection timings match each other to further remove effects of in-phase noise, the first magnetic detector 311 and the second magnetic detector 312 arranged in the conveyance direction one in front of the other.

In order to perform the differential processing, the first magnetic detector 311 and the second magnetic detector 312 need to output detection signals of the same level in the case where the first magnetic detector 311 and the second magnetic detector 312 detect a magnetic field of the same strength. Accordingly, for example, gain adjustment is performed in an amplifying unit 320 such that the strengths of the detection signals outputted from the first magnetic detector 311 and the second magnetic detector 312 are equal in the case where the same magnetic field is detected by the first magnetic detector 311 and the second magnetic detector 312.

Part (b) of FIG. 12 illustrates a configuration example of an analog circuit of the amplifying unit 320. The amplifying unit 320 includes a first amplifier 321 formed of an operational amplifier A1 and resistances r1, r2 and a second amplifier formed of an operational amplifier A2 and resistances r3, r4 and can adjust the strengths of the detection signals outputted from the first magnetic detector 311 and the second magnetic detector 312 by adjusting the resistances r1, r2, r3, and r4.

A signal obtained by the differential processing is converted from an analog value to a digital value by an AD convertor. The multiplication processing may be performed on the signal subjected to the AD conversion and a signal temporary stored in a memory after the AD conversion to be delayed by predetermined time Δt (formula 3).

Although the configuration in which the differential processing is achieved by the analog circuit is employed in the embodiment, a configuration in which the differential processing is digitally performed in the computation unit 330 may be employed. Moreover, the distance d between the first magnetic detector 311 and the second magnetic detector 312 in a y direction that is the conveyance direction is preferably such a distance that one of the magnetic detectors is arranged at a position about a half width of a peak away from the other magnetic detector, the peak obtained in the case where the other magnetic detector detects the detection signal of the magnetic foreign object contained in the inspection object 10.

Furthermore, the accuracy of the multiplication processing can be improved by removing disturbance noise of a low frequency component from the detection signals by using a high-pass filter. The high-pass filter may be an analog filter achieved by an electric circuit or a digital filter configured to digitally perform an operation.

In the first to fourth embodiments described above, the time correction of Δt is preferably performed based on the actual speed at which the inspection object 10 is actually conveyed on the conveyance route 101. Accordingly, it is preferable to calculate a time correction amount corresponding to the conveyance speed actually measured by, for example, detecting markers added to both end portions (portions where no inspection objects 10 are disposed), in the conveyance direction, of the conveyor belt forming the conveyance route 101 with an optical sensor or the like provided at a position facing the markers. In this configuration, an appropriate time correction amount can be calculated also in the case where the conveyance speed changes due to an effect of aging or the like and the detection accuracy of the magnetic foreign object can be easily maintained.

Note that the aforementioned conveyance speed detecting unit using the markers and the optical sensor is an example and the conveyance speed detecting unit may be any unit as long as it detects the conveyance speed of the inspection object 10 conveyed on the conveyance route 101. Accordingly, the conveyance speed may be calculated by providing drive amount detecting unit for detecting a drive amount (for example, a rotation amount of a motor) or the like of a drive source configured to drive the conveying unit in the conveyance route 101 and using the drive amount detecting unit as the conveyance speed detecting unit to perform the time correction. Moreover, the conveyance speed may be calculated by conveying markers on the conveyance route 101 together with the inspection object 10 and detecting these markers. Furthermore, the conveyance speed may be calculated from a predetermined parameter other than the aforementioned parameters of the inspection device or a device including the inspection device. For example, the time correction may be performed by using accumulated usage time of the device.

Fifth Embodiment

Figure 13:
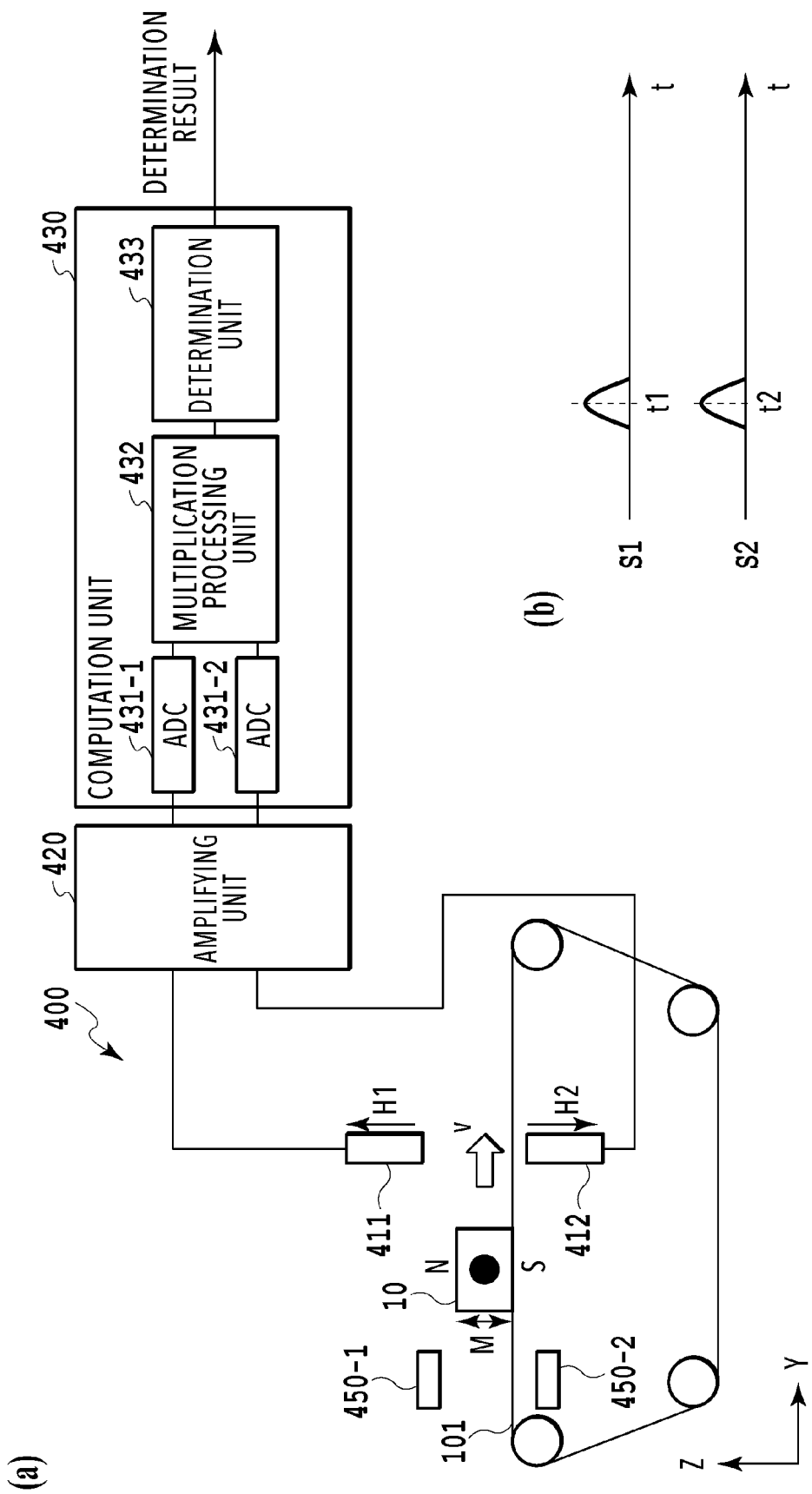
FIG. 13 is a schematic configuration diagram of an inspection device according to a fifth embodiment of the present invention.

FIG. 13 illustrates a configuration of an inspection device according to a fifth embodiment of the present invention. The inspection device 400 includes the conveyance route 101 that conveys the inspection object 10 at an arbitrary moving speed v and magnetizing unit 450 for magnetizing the inspection object 10 in a predetermined direction.

Moreover, an upper magnetic detector 411 provided above the conveyance route 101 and a lower magnetic detector 412 located to face the upper magnetic detector 411 with the conveyance route therebetween are arranged downstream of the magnetizing unit 450 in the conveyance direction, the upper magnetic detector 411 and the lower magnetic detector 412 configured to detect a magnetic field of a component in a direction perpendicular to the conveyance surface of the conveyance route 101 generated by remanent magnetization of the magnetic foreign object inside or near the inspection object 10.

Moreover, the inspection device 400 includes an amplifying unit 420 that amplifies the signals of the upper magnetic detector 411 and the lower magnetic detector 412 and a computation processing unit 430 that includes AD convertors 431 configured to convert the signals of the upper magnetic detector 411 and the lower magnetic detector 412 from analog values to digital values, a multiplication processing unit 432 configured to perform multiplication processing on the signals of the upper magnetic detector 411 and the lower magnetic detector 412, and a determination unit 433 configured to determine presence or absence of the magnetic foreign object.

In the configuration illustrated in FIG. 13, in order to simplify the description, it is assumed that each of the upper magnetic detector 411 and the lower magnetic detector 412 has one magnetic sensor and the magnetic sensors form a pair. The upper magnetic detector 411 is arranged height h away from the conveyance surface of the conveyance route 101 through which the inspection object 10 can pass. The lower magnetic detector 412 is arranged below the conveyance surface of the conveyance route 101 at a position facing the upper magnetic detector 411 with the conveyance route 101 therebetween.

In this case, the positions where the upper magnetic detector 411 and the lower magnetic detector 412 face each other need to satisfy the following conditions. First, the positions of the upper magnetic detector 411 and the lower magnetic detector 412 in the width direction (X direction) of the conveyance route 101 may be the same or different as long as both of the upper magnetic detector 411 and the lower magnetic detector 412 can simultaneously detect the magnetic field generated by the remanent magnetization of the same magnetic foreign object conveyed on the conveyance route 101.

The positions of the upper magnetic detector 411 and the lower magnetic detector 412 in the conveyance direction (Y direction) are preferably the same. Specifically, it is desirable that, in the detection signals, a timing at which the inspection object 10 comes closest to the upper magnetic detector 411 is substantially the same as a timing at which the inspection object 10 comes closest to the lower magnetic detector 412. However, since the magnetic field generated by the magnetic foreign object has certain width, the S/N ratio can be sufficiently improved as a result of simple multiplication processing as long as the arrangement is practical. In the case where the positions are shifted in the conveyance direction (Y direction), a following mode may be employed to further improve the accuracy: shifting of the positions of the upper and lower magnetic sensors in the conveyance direction is calculated by conveying a predetermined test medium or the like and the multiplication processing is performed with time correction performed to align the positions of the upper and lower magnetic sensors.

The positions of the upper magnetic detector 411 and the lower magnetic detector 412 in a direction (Z direction) perpendicular to the conveyance surface of the conveyance route 101 may be any positions as long as both of the upper magnetic detector 411 and the lower magnetic detector 412 can detect the magnetic field generated by the remanent magnetization of the same magnetic foreign object conveyed on the conveyance route 101. For example, the configuration may be such that the upper magnetic detector 411 and the lower magnetic detector 412 are formed of magnetic sensors of the same type and are arranged with the conveyance route 101 therebetween such that the detection regions thereof overlap each other in the Z direction.

Moreover, although the lower magnetic detector 412 may be located away from the conveyance surface of the conveyance route 101 at a distance as great as the height h, the lower magnetic detector 412 is preferably arranged as close to the conveyance surface as possible below the conveyance surface and this is prominent particularly in the case where the upper magnetic detector 411 and the lower magnetic detector 412 are formed of the magnetic sensors of the same type and have the same magnetic characteristics. However, it is only necessary that the lower magnetic detector 412 can detect the magnetic field generated by the remanent magnetization of the magnetic foreign object at the same timing as the upper magnetic detector 411 as described above, and the lower magnetic detector 412 may be located away from the conveyance surface at a distance greater or smaller than the height h.

The upper magnetic detector 411 and the lower magnetic detector 412 preferably have the same magnetic characteristics and it desirable that, even if the heights of the detection waveforms for the same detection target are different, at least time t1 and time t2 at which the waveforms reach the peaks are substantially the same (refer to FIG. 13). In other words, the timings at which the inspection object 10 comes closest to the respective magnetic detectors are desirably the same. Moreover, in the case where the upper magnetic detector 411 and the lower magnetic detector 412 are arranged such that magnetic field detection directions H1, H2 thereof coincide with directions perpendicular to the conveyance surface of the conveyance route 101, detection polarities become stable, independent of a dead band and the passing position of the magnetic foreign object.

The conveyance route 101 may be conveying unit for conveying the inspection object 10 at predetermined speed such as, for example, a conveyor belt or a slider. The inspection object 10 may be a powder or granular object, a small piece, or in a form wrapped in a packaging material such as a bag or a box. Note that the packaging material is made of a non-magnetic material. The magnetic foreign object is contained inside or near the inspection object, is assumed to be a piece of rust, a screw, a fragment of a blade, or the like, and contains a magnetic material.

In the case of detecting a fine magnetic foreign object, the inspection device 400 desirably includes the magnetizing unit 450 for magnetizing the magnetic foreign object contained in the inspection object 10. The magnetizing unit 450 is arranged upstream of the upper magnetic detector 411 and the lower magnetic detector 412 in the conveyance route 101. The magnetizing unit 450 is formed of members such as magnets fixed above and below the conveyance route 101 such that the inspection object 10 can pass. A magnetizing direction M in which the inspection object 10 is magnetized may be any direction but it is desirable that the inspection object 10 is magnetized such that components in the same directions as the magnetic field detection directions of the magnetic detectors are made stronger. If the magnetizing direction is set to the direction perpendicular to the conveyance surface of the conveyance route 101, the magnetizing direction coincides with the detection directions of the upper magnetic detector 411 and the lower magnetic detector 412 and more accurate detection can be thus performed. Note that, in the case where the remanent magnetization of the magnetic foreign object is sufficiently large, the magnetizing unit 450 is unnecessary.

In this case, in the embodiment, Z-direction components of the magnetic field generated by the remanent magnetization of the magnetic foreign object and detected by the upper magnetic detector 411 and the lower magnetic detector 412 are applied to the respective detectors in opposite polarity directions. Specifically, in the case of FIG. 13, the arrangement is such that the magnetic field is applied to the upper magnetic detector 411 with the Z component direction being a positive direction while the magnetic field is applied to the lower magnetic detector 412 with the Z component direction being a negative direction. The upper magnetic detector 411 and the lower magnetic detector 412 are arranged such that the magnetic field detection directions thereof are opposite to each other with respect to the conveyance route 101 to be capable of accurately detecting the magnetic field. Although the magnetization direction M is illustrated such that an upper portion of the magnetic foreign object is the north pole and the lower portion of the magnetic foreign object is the south pole in FIG. 13, in the case where the magnetization direction M of the magnetic foreign object is such that the polarities are reversed, the directions of the magnetic field applied to the upper magnetic detector 411 and the lower magnetic detector 412 are also reversed.

The upper magnetic detector 411 and the lower magnetic detector 412 may constantly perform the detection operation or may perform the detection operation only at the passing timings of the inspection objects 10. For example, the configuration may be such that another supply device that supplies the inspection objects 10 to the inspection device 400 according to the embodiment transmits information including supplying timing information of the inspection objects 10 to a not-illustrated control unit and the upper magnetic detector 411 and the lower magnetic detector 412 perform the detection operation only at the timings at which the inspection objects 10 pass, based on the supply timing information. Note that the other supplying device that supplies the inspection objects 10 may be configured to be integral with the inspection device 400. Furthermore, performing the detection operation only at the timings at which the inspection objects 10 pass includes executing the detection operation with margins of a predetermined time provided before and after each timing at which the inspection object 10 passes such that this timing is included in the detection operation.

Figure 14:
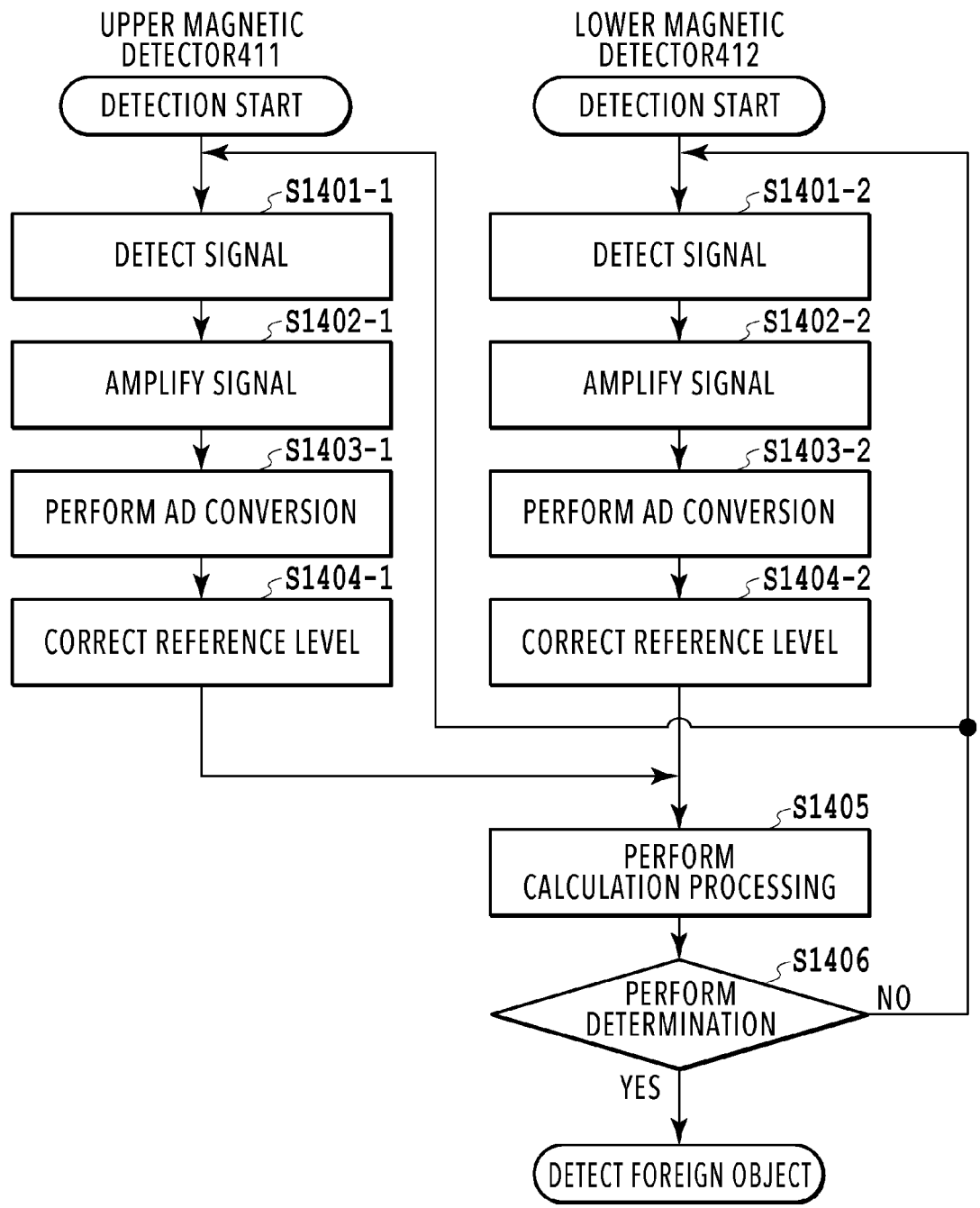
FIG. 14 is a flowchart illustrating processing of detecting the magnetic foreign object in the inspection device according to the fifth embodiment of the present invention.

FIG. 14 illustrates a flowchart explaining a method of processing the detection signals in the inspection device 400 according to the fifth embodiment of the present invention. First, the upper magnetic detector 411 and the lower magnetic detector 412 start detection of the magnetic field and output signals based on detection results (step S1401-1, step 1401-2).

The outputted signals are amplified in the amplifying unit 420 (step S1402-1, step S1402-2) and digitized into digital values in the AD convertors 431 of the computation processing unit 430 (step S1403-1, step S1403-2). This amplification may be DC amplification. However, performing AC amplification enables removal of a DC magnetic field component of geomagnetism and the like. A DC component may be removed after the AD conversion or removed in the circuit before the AD conversion.

Next, in the computation processing unit 430, level correction is performed on the detection signal S1 of the upper magnetic detector 411 and the detection signal S2 of the lower magnetic detector 412 subjected to the AD conversion such that reference levels of the respective signals become zero (S1404-1, S1404-2). As in the first embodiment, the level correction is performing numerical value correction on the reference levels such that the detection signal S1 fluctuates around zero, and can be performed by subtracting an average value of the detection signal in the period where there is no inspection object (t'1≤t'≤t'2) from the detection signal but may be performed by using another method.

Next, in the multiplication processing unit 432, the multiplication processing is performed on the detection signal S1 of the upper magnetic detector 411 and the detection signal S2 of the lower magnetic detector 412 subjected to the level correction (step S1405). In the result of the multiplication processing, the phase in the case where the magnetic foreign object is detected and the phase in the case where the noise component is detected are in the reverse phase relationship. Specifically, as illustrated in part (b) of FIG. 15, in the result of the multiplication processing (S1×S2), a detection signal component detecting the remanent magnetization of the magnetic foreign object swings in the positive direction while a signal component detecting the noise component swings in the negative direction.

The direction of the magnetic field generated by the remanent magnetization of the magnetic foreign object and applied to each of the upper magnetic detector 411 and the lower magnetic detector 412 and the direction of an uniform disturbance magnetic field applied to each of the upper magnetic detector 411 and the lower magnetic detector 412 are the same in one of the upper magnetic detector 411 and the lower magnetic detector 412 and are different in the other one. Accordingly, in the result of the multiplication processing, the component detecting the magnetic foreign object and the component of the disturbance magnetic field are in a reverse phase relationship. Thus, in the result of the multiplication processing, the signal detecting the magnetic foreign object is present only on one of the positive side or the negative side and the signal detecting the noise component and the signal detecting the magnetic foreign object have the opposite polarities (swing in the opposite directions).

Furthermore, since the polarities of noise generated from the magnetic detectors themselves and noise generated from a circuit board randomly change, the possibility of the phases of these noises being the same as that of the signal detecting the magnetic foreign object is low and these noises are substantially signals changing asynchronously. Accordingly, multiplication results of randomly changing noise components have the opposite polarity to the signal detecting the magnetic foreign object.

Thus, a threshold for detecting the magnetic foreign object needs to be set only on one of the positive side and the negative side and the inspection device 400 can determine that the magnetic foreign object is detected if the multiplication result exceeds the predetermined threshold.

Figure 15:
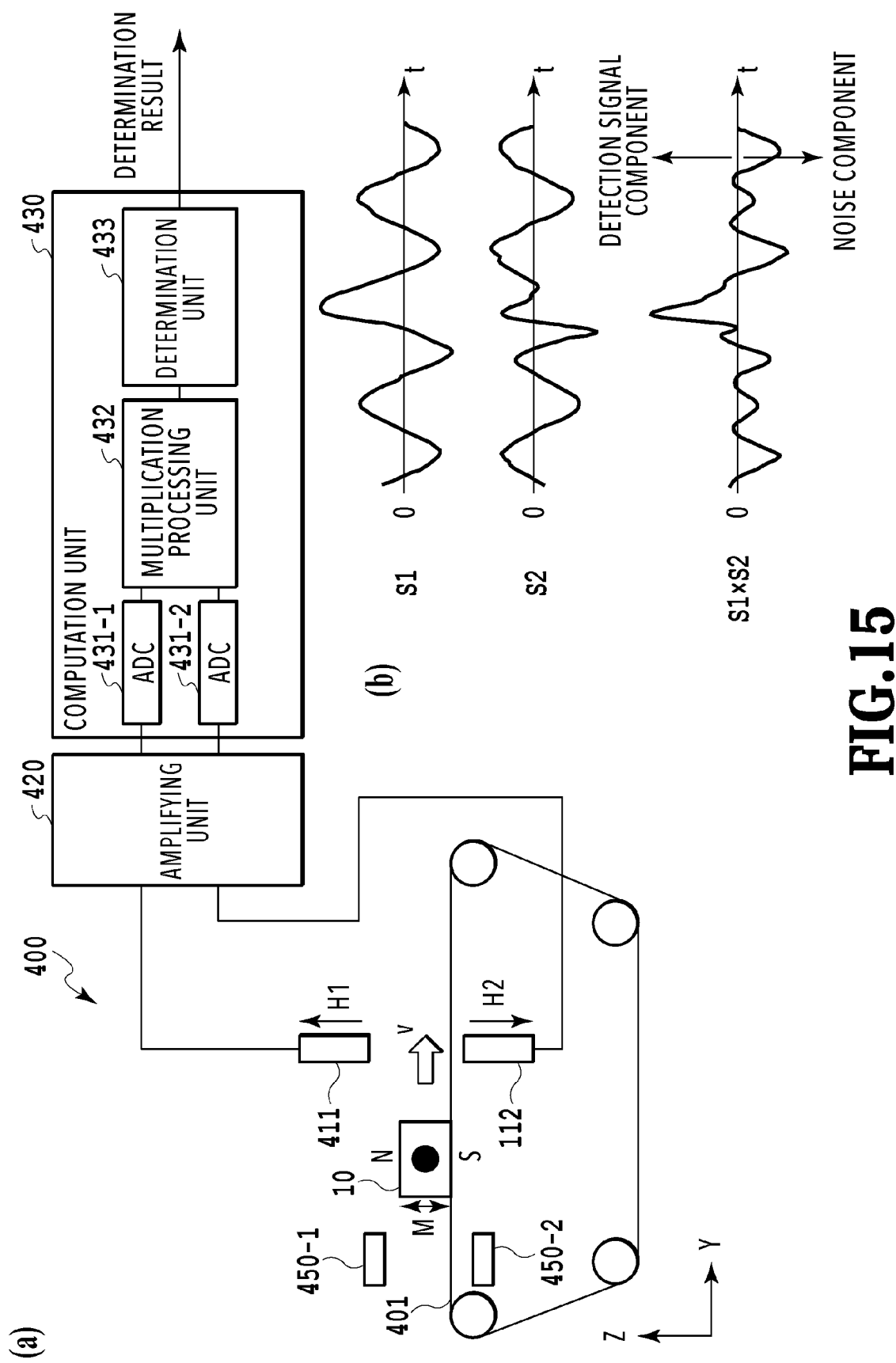
FIG. 15 includes a configuration diagram of the inspection device according to the fifth embodiment of the present invention and graphs of detection signals.

The polarity of the detection signal of the magnetic foreign object subjected to the multiplication processing depends on the phase relationship between the detection signals S1 and S2 of the upper magnetic detector 411 and the lower magnetic detector 412 before the multiplication processing. In the embodiment, since the magnetic field detection directions of the upper magnetic detector 411 and the lower magnetic detector 412 are opposite to each other as illustrated in FIG. 15, the signals before the multiplication processing obtained in the case where the magnetic foreign object is detected fluctuate in the same phase and the multiplication processing result has the positive polarity. Moreover, the multiplication processing result of the noise component has the negative polarity.

Figure 16:
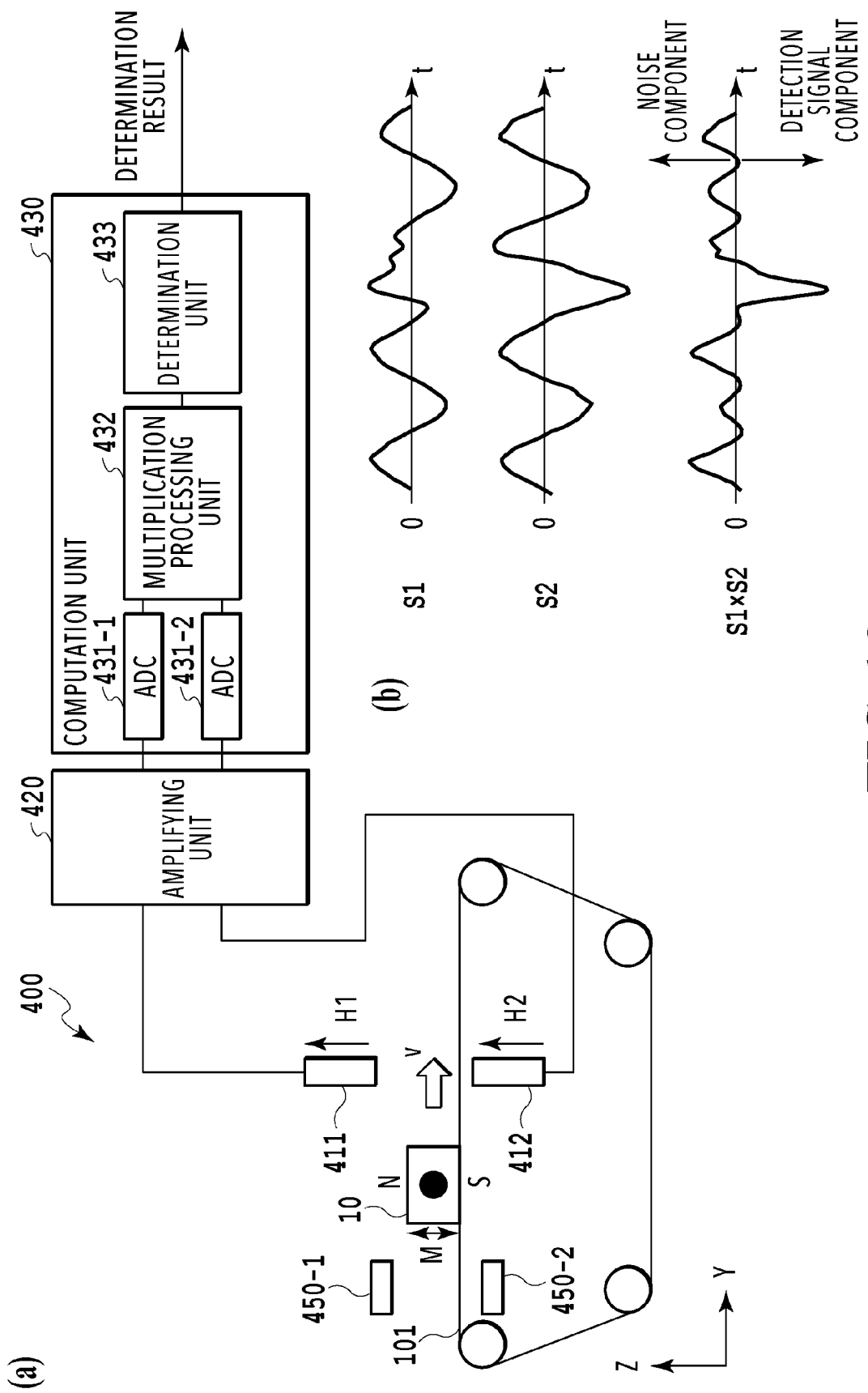
FIG. 16 includes a configuration diagram illustrating another mode of the inspection device according to the fifth embodiment of the present invention and graphs of detection signals.

Meanwhile, in the case where the upper magnetic detector 411 and the lower magnetic detector 412 are arranged such that the magnetic field detection directions thereof coincide with each other as illustrated in FIG. 16, the signals before the multiplication processing obtained in the case where the magnetic foreign object is detected fluctuate in the opposite phases and the multiplication processing result has the negative polarity. In this case, the multiplication processing result of the noise component has the positive polarity.

The multiplication processing result obtained in the case where the magnetic foreign object is detected may be made to have a desired polarity by adjusting the phase relationships between the detection signals S1 and S2 of the upper magnetic detector 411 and the lower magnetic detector 412 before the multiplication processing. The method of adjusting the phases may be achieved by using, for example, an inverting amplifier or by digitally inverting the polarity.

Executing the multiplication processing as described above allows the noise signal and the magnetic foreign object detection signal to be separated from each other based on a synchronous relationship of the detection signals irrespective of the magnetic detection sensitivities of the upper magnetic detector 411 and the lower magnetic detector 412 and a difference in the peak value between the noise component and the signal component detecting the magnetic foreign object can be increased. Thus, the S/N ratio is clearly improved.

A threshold set in advance may be used to determine the signal component detecting the magnetic foreign object in the arrangement in which the multiplication processing result obtained in the detection of the magnetic foreign object takes one of the polarities (FIG. 15). Specifically, in the example of FIG. 15, the multiplication processing result obtained in the case where the magnetic foreign object is detected takes the positive polarity but multiplication processing results with the positive polarity include results in which noise components due to the disturbance magnetic field incidentally give the positive polarity. However, these multiplication processing results due to the noise components are smaller than the multiplication processing result obtained in the case where the magnetic foreign object is detected. Thus, it is preferable that the multiplication processing result lower than the threshold set in advance are determined as the noise component due to disturbance magnetic field and only the multiplication processing result equal to or greater than the threshold is determined as the signal component detecting the magnetic foreign object. In the arrangement in which the multiplication processing result obtained in the detection of the magnetic foreign object takes the negative polarity (FIG. 16), only the multiplication processing result equal to or lower than a threshold set in advance is determined as the signal component detecting the magnetic foreign object.

In step S1406 of FIG. 14, the aforementioned determination is performed to determine whether the inspection object 10 contains the magnetic foreign object.

In the case where the magnetic foreign object is detected, the processing such as removing the inspection object 10 containing the magnetic foreign object from the conveyance route 101 may be performed. Moreover, the inspection device 400 may include an alarm unit and give an alarm while taking measures such as stopping the conveyance in the conveyance route.

Furthermore, the averaging processing may be performed on each of the signals to be subjected to the multiplication processing to round the noise and thereby improve the S/N ratio of the multiplication processing result. The averaging processing may be moving average, arithmetic mean, or the like. Note that the averaging processing may be performed on the multiplication processing result.

Figure 17:
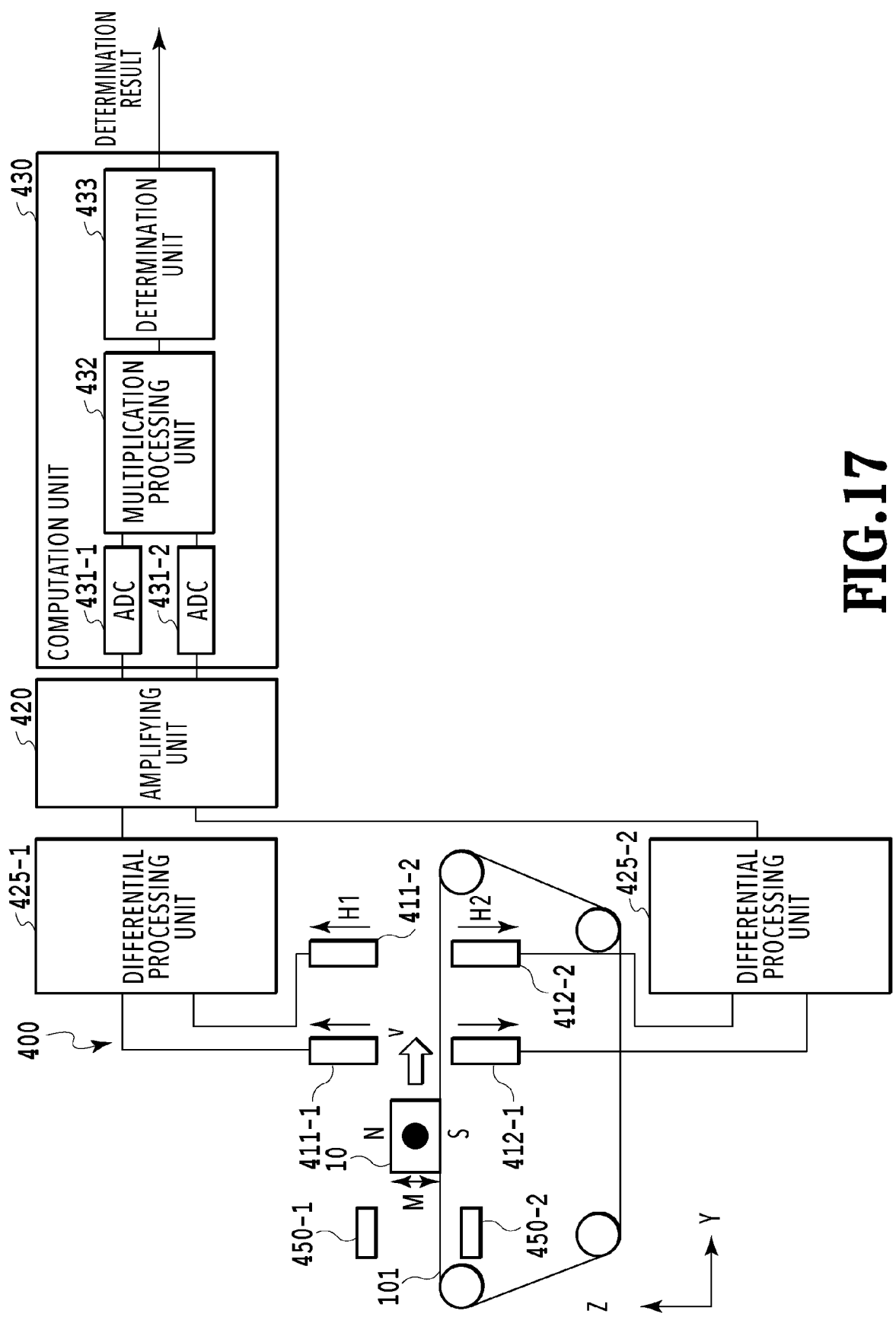
FIG. 17 is a schematic configuration diagram illustrating another mode of the inspection device according to the fifth embodiment of the present invention.

In the case where disturbance noise of a component with a lower frequency than the detection signal of the magnetic foreign object causes the reference level of values of signals to be subjected to the multiplication processing to be shifted from zero, this noise may cause degrading of the S/N ratio of the multiplication processing result. Accordingly, as illustrated in FIG. 17, the following configuration may be employed: two magnetic detectors are arranged as each of the upper magnetic detector 411 and the lower magnetic detector 412 and differential processing is performed on detection signals from the magnetic detectors arranged on the same side to remove disturbance noises fluctuating in the same phase. Then, the level correction is performed on the signals from which the disturbance noise is removed as in the first embodiment and the thus-obtained signals of the upper magnetic detector 411 and the signals of the lower magnetic detector 412 may be subjected to the multiplication processing or a signal of the low frequency component may be removed from the detection signals by using a high-pass filter. The differential processing may be performed in a circuit or digitally performed in a computation unit. The high-pass filter may be an analog filter achieved by an electric circuit or a digital filter configured to digitally remove the signal of the component with a lower frequency than the detection signal of the magnetic foreign object.

Note that, as described above, the magnetic detection sensitivities of the upper magnetic detector 411 and the lower magnetic detector 412 do not have to be the same. Since the determination of the noise by the multiplication processing is made based on the phase relationship between the signals of the upper magnetic detector 411 and the lower magnetic detector 412, adjustment of the magnetic detection sensitivities for the disturbance noise is unnecessary and whether a signal is the signal of the magnetic foreign object or the signal of the noise can be determined depending on the phase of the multiplication processing result.

In the case where the positions of the upper magnetic detector 411 and the lower magnetic detector 412 in the conveyance direction are shifted, time correction may be performed on the signals before the multiplication processing. However, in the case where a time gap between the detection signals for the magnetic field generated by the remanent magnetization of the magnetic foreign object in the upper magnetic detector 411 and the lower magnetic detector 412 is very small, the time correction is unnecessary. Omitting the time correction can improve response of detecting the magnetic foreign object and simplify the multiplication processing. The case where the time gap between the detection signals is very small may be the case where the gap is such a degree that the upper magnetic detector 411 and the lower magnetic detector 412 simultaneously detects part of the magnetic field generated by the remanent magnetization of the magnetic foreign object and, for example, it is only necessary that detection regions of the upper magnetic detector 411 and the lower magnetic detector 412 overlap each other in the Y direction as described above.

In the present invention, the conveyance speed at which the inspection object is conveyed may be predetermined constant speed v or any speed that changes as in the case where the inspection object is moved by using a slider or the like.

Moreover, the inspection device 400 may include a display unit used to present the multiplication result of the detection signals to the user. The user can directly determine presence or absence of the magnetic foreign object from the multiplication result in addition to the determination by the determination unit.

Furthermore, the inspection device 400 may include magnetic shielding unit 440 made of a high magnetic permeability material to shield effects of the disturbance noise. The magnetic shielding unit 440 is configured such that a surface facing the conveyance route 101 is open and the other five surfaces are made of the high magnetic permeability material to cover the upper magnetic detector 411 and the lower magnetic detector 412. Providing the magnetic shielding unit 440 can reduce the effects of the disturbance noise entering the upper magnetic detector 411 and the lower magnetic detector 412 and improve the S/N ratio. The high magnetic permeability material may be permalloy, silicon steel plate, or the like.

Sixth Embodiment

Figure 18:
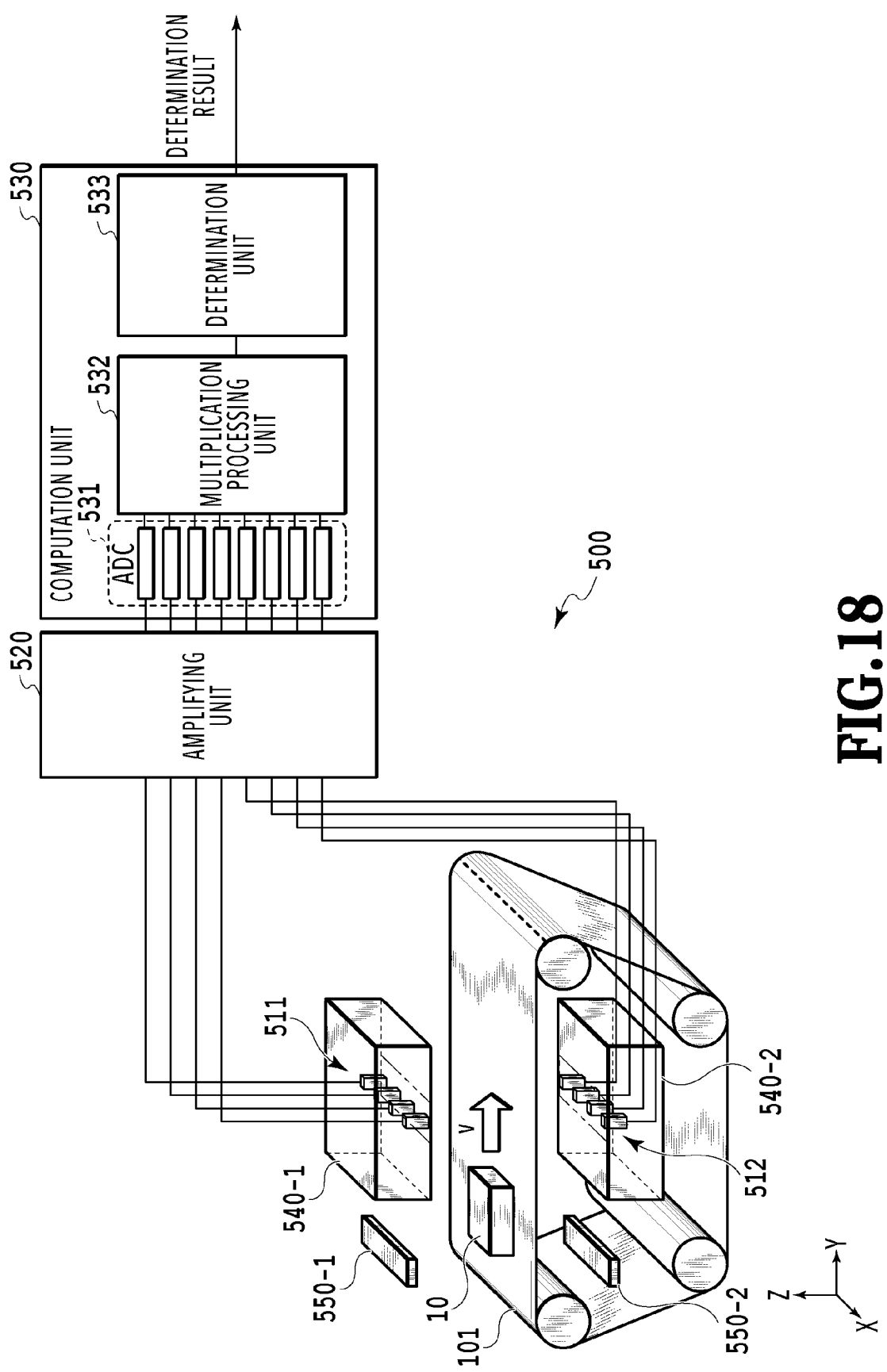
FIG. 18 is a schematic configuration diagram of an inspection device according to a sixth embodiment of the present invention.

FIG. 18 illustrates a configuration of an inspection device 500 according to a sixth embodiment of the present invention. In the sixth embodiment, a configuration that improves the detection accuracy in the width direction of the conveyance route is described. Description of contents that are the same as those in the fifth embodiment is omitted.

In the fifth embodiment, description is given of an example of the configuration in which one upper magnetic 411 and one lower magnetic detector 412 are arranged. Meanwhile, in this embodiment, at least one of the upper magnetic detector 511 and the lower magnetic detector 512 includes multiple magnetic detectors in the width direction of the conveyance unit.

First, description is given of the case where the number of magnetic detectors forming the upper magnetic detector 511 and the number of magnetic detectors forming the lower magnetic detector 512 are the same.

As illustrated in FIG. 18, the upper magnetic detector 511 including multiple magnetic detectors arranged in the width direction of the conveyance route 101 is provided above the conveyance route 101. The magnetic detectors forming the upper magnetic detector 511 may be linearly arranged in the width direction of the conveyance route 101 or arranged in a curved shape such as an S shape or an arc shape. The lower magnetic detector 512 including multiple magnetic detectors arranged in the width direction of the conveyance route 101 is provided at a position facing the upper magnetic detector 511 with the conveyance route 101 therebetween.

Signals of the magnetic detectors forming the upper magnetic detector 511 and the lower magnetic detector 512 are amplified in an amplifying unit 520 and inputted into an AD convertor 531 to be digitized into digital values. This amplification may be DC amplification. However, performing AC amplification enables removal of a DC magnetic field component of geomagnetism and the like. A DC component may be removed after the AD conversion or removed in the circuit before the AD conversion.

The signals converted to the digital values are subjected to level correction such that reference levels of the signals become zero as in the first embodiment. The multiplication processing unit 532 performs multiplication processing on the signals of the upper magnetic detector 511 and the lower magnetic detector 512 subjected to the level correction. In this case, the multiplication processing may be performed on the detection signals of each pair of upper and lower magnetic detectors in the upper magnetic detector 511 and the lower magnetic detector 512 or performed on a signal obtained by adding up the signals of the magnetic detectors in the upper magnetic detector 511 and a signal obtained by adding up the signals of the magnetic detectors in the lower magnetic detector 512.

In the case where the multiplication processing is to be performed on the signals of each pair of magnetic detectors forming the upper magnetic detector 511 and the lower magnetic detector 512, the passing position of the magnetic foreign object in the width direction in the conveyance route 101 can be determined depending on the pair of the magnetic detectors detecting the magnetic foreign object and the pair of the magnetic detectors providing the greatest multiplication result.

Figure 19:
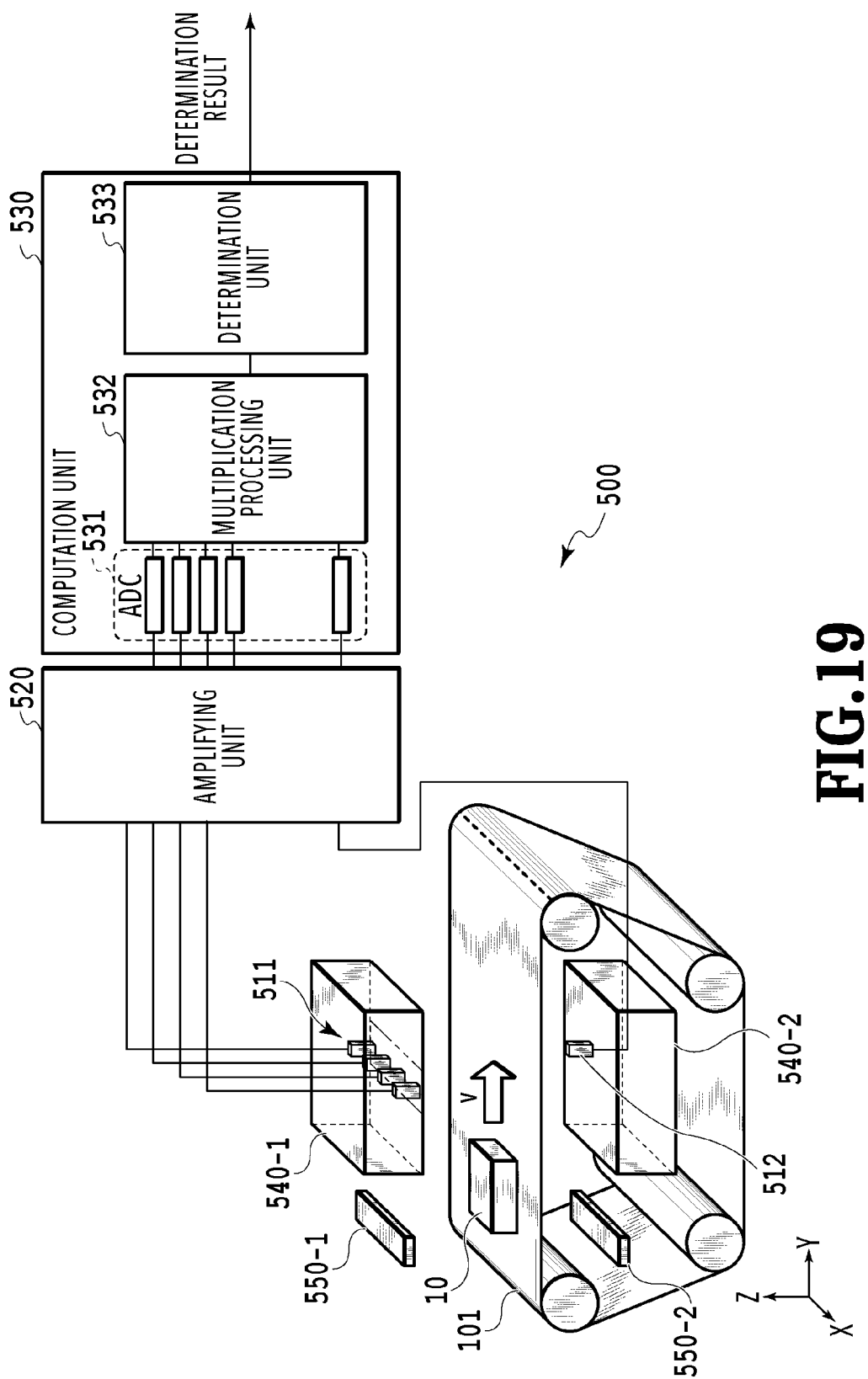
FIG. 19 is a schematic configuration diagram illustrating another mode of the inspection device according to the sixth embodiment of the present invention.

Next, as another mode of the embodiment, description is given of the case where the number of magnetic detectors forming the upper magnetic detector 511 is different from the number of magnetic detectors forming the lower magnetic detector 512. In other words, the number of used magnetic detectors can be reduced. Description is given of an example in which four magnetic detectors form the upper magnetic detector 511 and one magnetic detector forms the lower magnetic detector 512 as illustrated in FIG. 19.

The multiple magnetic detectors forming the upper magnetic detector 511 are arranged in the width direction of the conveyance route. The lower magnetic detector 512 is arranged substantially at the middle of the magnetic detectors forming the upper magnetic detector 511 in the width direction of the conveyance route 101 and is arranged substantially at the middle of the magnetic detectors forming the upper magnetic detector also in the conveyance direction.

Signals of the magnetic detectors forming the upper magnetic detector 511 and the lower magnetic detector 512 are amplified in the amplifying unit 520 and inputted into the AD convertor 531 to be digitized into digital values. This amplification may be DC amplification. However, performing AC amplification enables removal of a DC magnetic field component of geomagnetism and the like. A DC component may be removed after the AD conversion or removed in the circuit before the AD conversion.

The signals converted to the digital values are subjected to the level correction such that reference levels of the signals become zero. The multiplication processing unit 532 performs multiplication processing on the signals of the upper magnetic detector 511 and the lower magnetic detector 512 subjected to the level correction. A signal obtained by adding up the signals of the magnetic detectors forming the upper magnetic detector 511 and the signal detected by the magnetic detector in the lower magnetic detector 512 may be multiplied or the multiplication processing may be performed on the signal of the magnetic detector forming the lower magnetic detector 512 and the signal of each of the magnetic detectors forming the upper magnetic detector 511.

The arrangement, number, and configuration of the magnetic detectors may be determined such that one of the magnetic detectors forming the upper magnetic detector 511 and one of the magnetic detectors forming the lower magnetic detector 512 can detect passing of the magnetic foreign object in a range in which the magnetic foreign object can pass in the width direction of the conveyance route 101.

Moreover, as illustrated in FIGS. 18 and 19, the inspection device 500 may include magnetic shielding unit 540 made of a high magnetic permeability material to shield effects of disturbance noise. The magnetic shielding unit 540 is configured such that a surface facing the conveyance route 101 is open and the other five surfaces are made of the high magnetic permeability material to cover the upper magnetic detector 511 and the lower magnetic detector 512. Providing the magnetic shielding unit 540 can reduce the effects of the disturbance noise entering the upper magnetic detector 511 and the lower magnetic detector 512 and improve the S/N ratio. The high magnetic permeability material may be permalloy, silicon steel plate, or the like.

Seventh Embodiment

Figure 20:
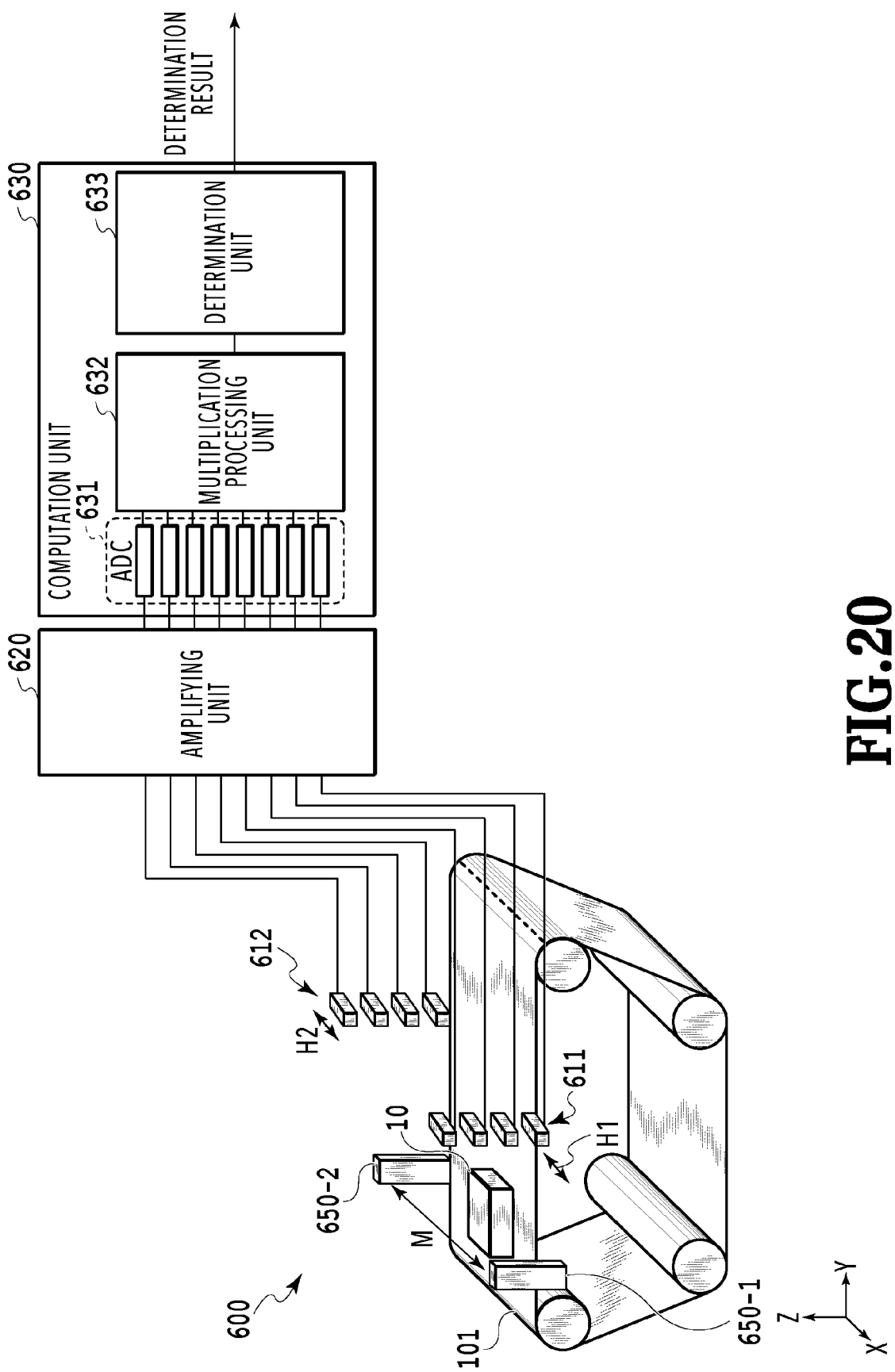
FIG. 20 is a schematic configuration diagram of an inspection device according to a seventh embodiment of the present invention.

FIG. 20 illustrates a configuration of an inspection device 600 according to a seventh embodiment of the present invention. In the seventh embodiment, description is given of a configuration in which a right magnetic detector 611 and a left magnetic detector 612 that are paired magnetic detectors are arranged at both ends of the conveyance route 101 in the width direction. The right magnetic detector 611 and the left magnetic detector 612 described in the embodiment correspond to the upper magnetic detector 511 and the lower magnetic detector 512 in the aforementioned embodiments but arrangement thereof is changed. Description of contents that are the same as those in the fifth and sixth embodiments is omitted.

In FIG. 20, the magnetic detectors are arranged at both ends of the conveyance route 101 in the width direction. In this configuration, since the magnetic detectors do not have to be arranged at a height low enough perform the detection of the conveyance surface, the height limit of the inspection object can be eliminated.

At least one pair of magnetic detectors whose magnetic field detection directions coincide with the width direction of the conveyance route 101 are arranged at positions at both ends of the conveyance route in the width direction to face each other with the conveyance route therebetween. The distance between the pair of magnetic detectors in the width direction of the conveyance route is set such that ranges in which the respective magnetic detectors can detect the magnetic foreign object overlap each other. Moreover, arrangement of the magnetic detectors in the Z direction is preferably determined according to a position where the magnetic foreign object is assumed to pass. In the case where a Z-direction range in which the magnetic foreign object is assumed to pass is large, multiple magnetic detectors are preferably installed in the Z direction as illustrated in FIG. 20.

In the case where multiple magnetic detectors are arranged in the Z direction, the number of magnetic sensors included in the right magnetic detector 611 and the number of magnetic sensors included in the left magnetic detector 612 facing the right magnetic detector 611 do not have to be the same. In this case, the signals of the magnetic detectors on each side may be subjected to adding processing and subjected to multiplication processing.

In the case of detecting a fine magnetic foreign object, the inspection device 600 desirably includes magnetizing unit 650 for magnetizing the inspection object 10. The magnetizing unit 650 is arranged upstream of the magnetic detectors in the conveyance route 101. The magnetizing unit 650 is formed of members such as magnets fixed such that the inspection object 10 can pass. A magnetizing direction M in which the inspection object 10 is magnetized may be any direction but the magnetic foreign object can be more accurately detected by being strongly magnetized in the width direction of the conveyance route 101 such that components in the same directions as the magnetic field detection directions of the magnetic detectors are made stronger. Note that, in the case where the remanent magnetization of the magnetic foreign object is sufficiently large, the magnetizing unit 650 is unnecessary.

Figure 21:
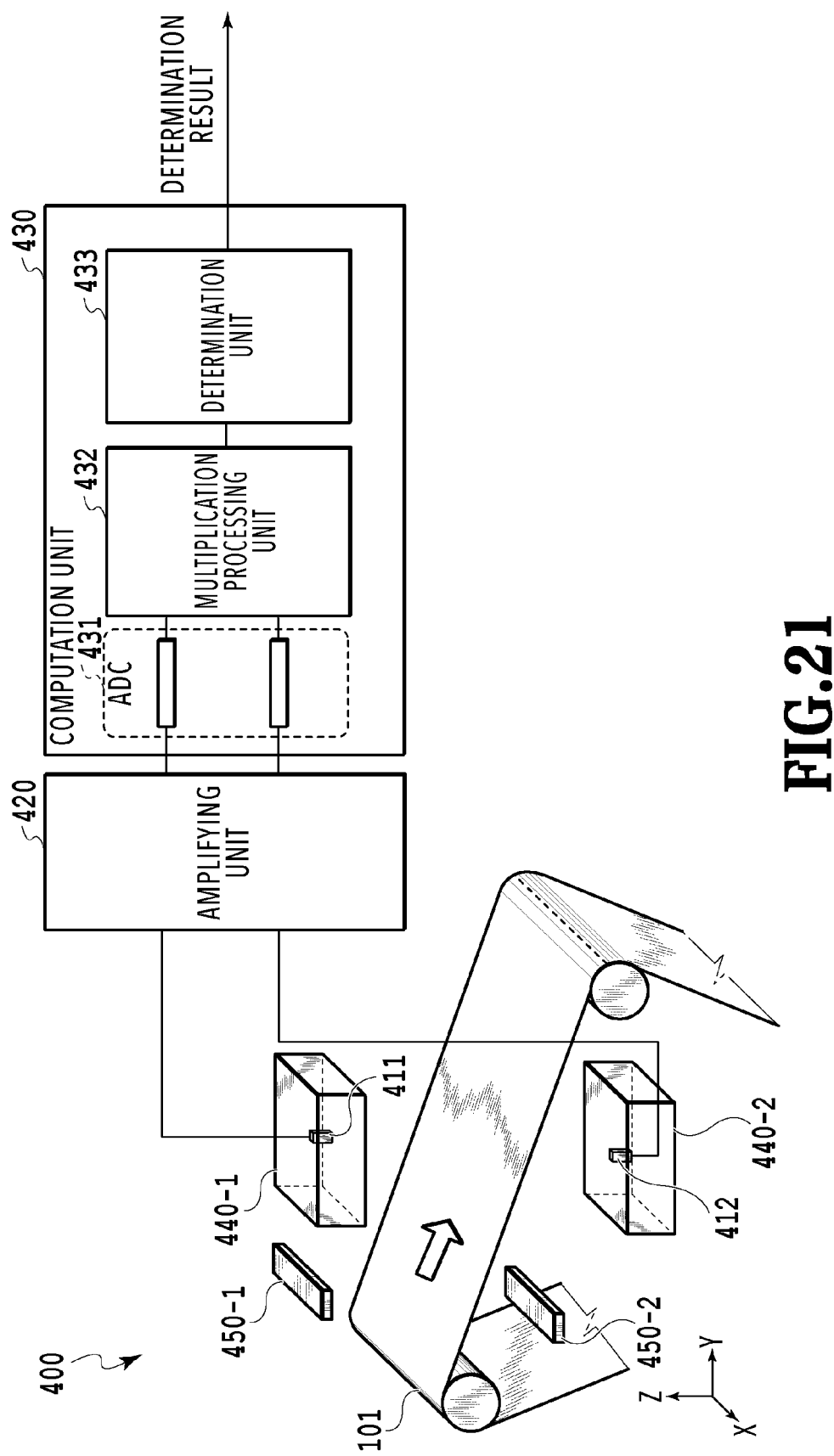
FIG. 21 is a schematic configuration diagram illustrating another mode of the inspection device according to the fifth embodiment of the present invention.

In the embodiments described above, the conveyance direction of the conveyance route 101 does not have to be a direction orthogonal to the magnetic field detection directions of the upper magnetic detector 411 and the lower magnetic detector 412. As illustrated in FIG. 21, the conveyance direction of the conveyance route 101 may have a Z-direction component with respect to the upper magnetic detector 411 and the lower magnetic detector 412 arranged such that the magnetic field detection directions thereof coincide with the Z direction. In this case, the magnetizing direction M of the magnetizing unit 450 preferably coincides with the Z direction that is the magnetic field detection directions of the upper magnetic detector 411 and the lower magnetic detector 412.

In the fifth to seventh embodiments described above, the inspection device only needs to include a pair of magnetic detectors arranged to face each other with a space where the inspection object 10 passes arranged therebetween and to be capable of simultaneously detecting the magnetic field of the predetermined component generated by the remanent magnetization of the magnetic foreign object contained inside or near the inspection object 10. Performing the multiplication processing on the detection signals detected by the pair of magnetic detectors allows the signal component of the noise and the signal component of the remanent magnetization of the magnetic foreign object to be separated from each other.

Eighth Embodiment

Description is given above of the case where the magnetization direction of the magnetic foreign object coincides with the magnetic field detection directions of the magnetic sensors forming the first magnetic detector and the second magnetic detector. However, there is a case where, in the magnetization of the magnetic foreign object, the magnetization direction of the magnetic foreign object is tilted with respect to the magnetic field detection directions of the magnetic sensors and does not coincide with the magnetic field detection direction of each magnetic sensor. For example, there is a case where, even if the magnetizing unit is arranged such that the magnetizing direction of the magnetic foreign object coincides with the magnetic field detection direction, the direction of the magnetic field applied to the magnetic foreign object is tilted in passing of the magnetic foreign object through the magnetic field generated by the magnetizing unit and the actual magnetizing direction is tilted with respect to the magnetic field detection direction. As illustrated in part (a) of FIG. 22, in a waveform of a detection signal obtained in this state by using a fluxgate sensor as the magnetic sensor, the phase turns and the polarity reverses at a position directly below the magnetic sensor MS and the waveform has peaks on the upper and lower sides. Due to this, the S/N ratio of the detection signal decreases.

Figure 22:
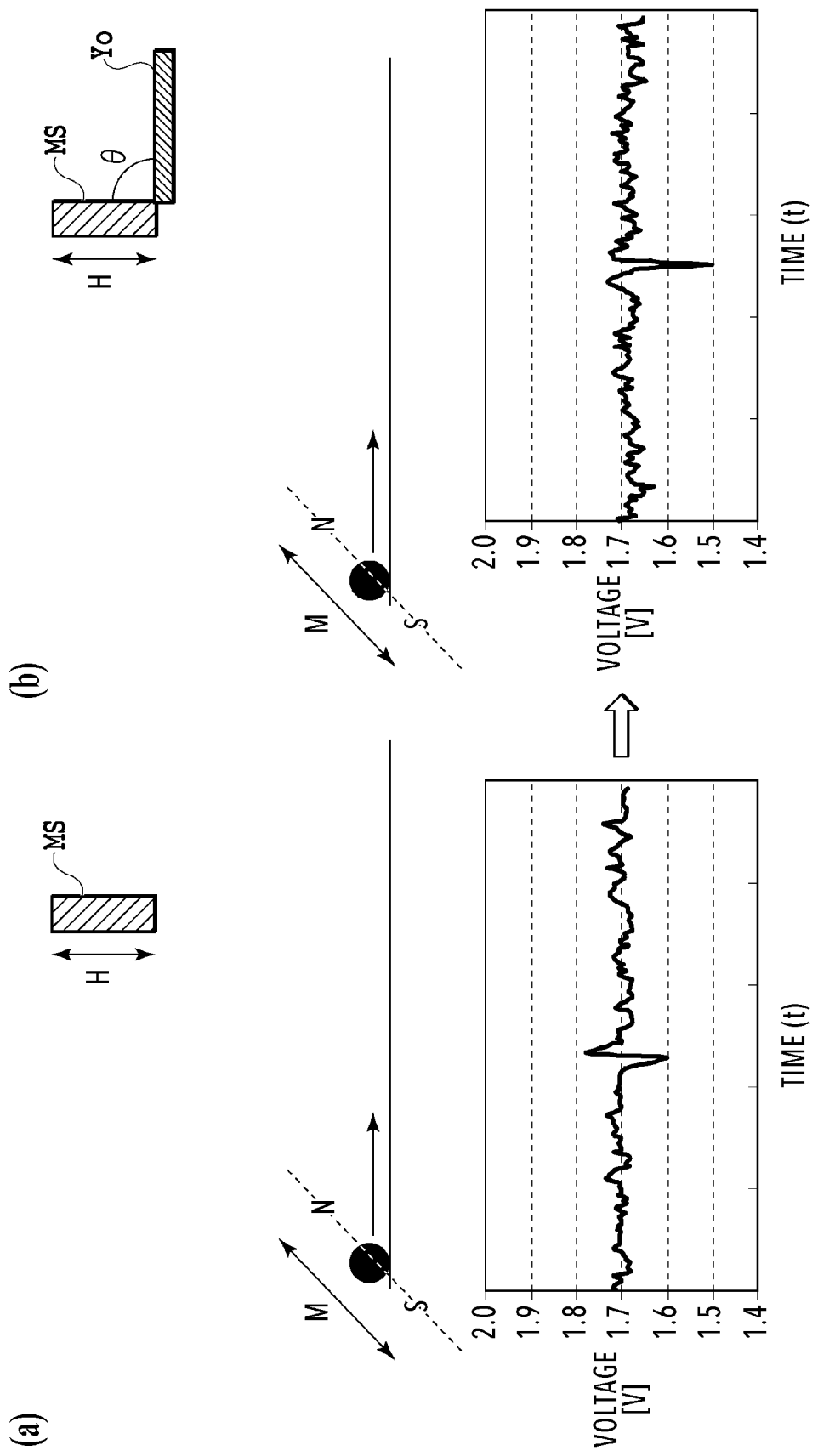
FIG. 22 includes configuration diagrams each illustrating part of an inspection device according to an eighth embodiment of the present invention and graphs of detection signals.

Accordingly, in this embodiment, as illustrated in part (b) of FIG. 22, a yoke Yo made of a magnetic material with high magnetic permeability is arranged near an end portion of the magnetic sensor MS such that an angle θ formed between the magnetic sensor MS and the yoke Yo is 90 degrees. Then, a waveform with a peak on one side as in the case where the magnetizing direction of the magnetic foreign object coincides with the magnetic field detection direction of the magnetic sensor is obtained due to a phase adjustment effect of the yoke Yo to be described later.

Figure 23:
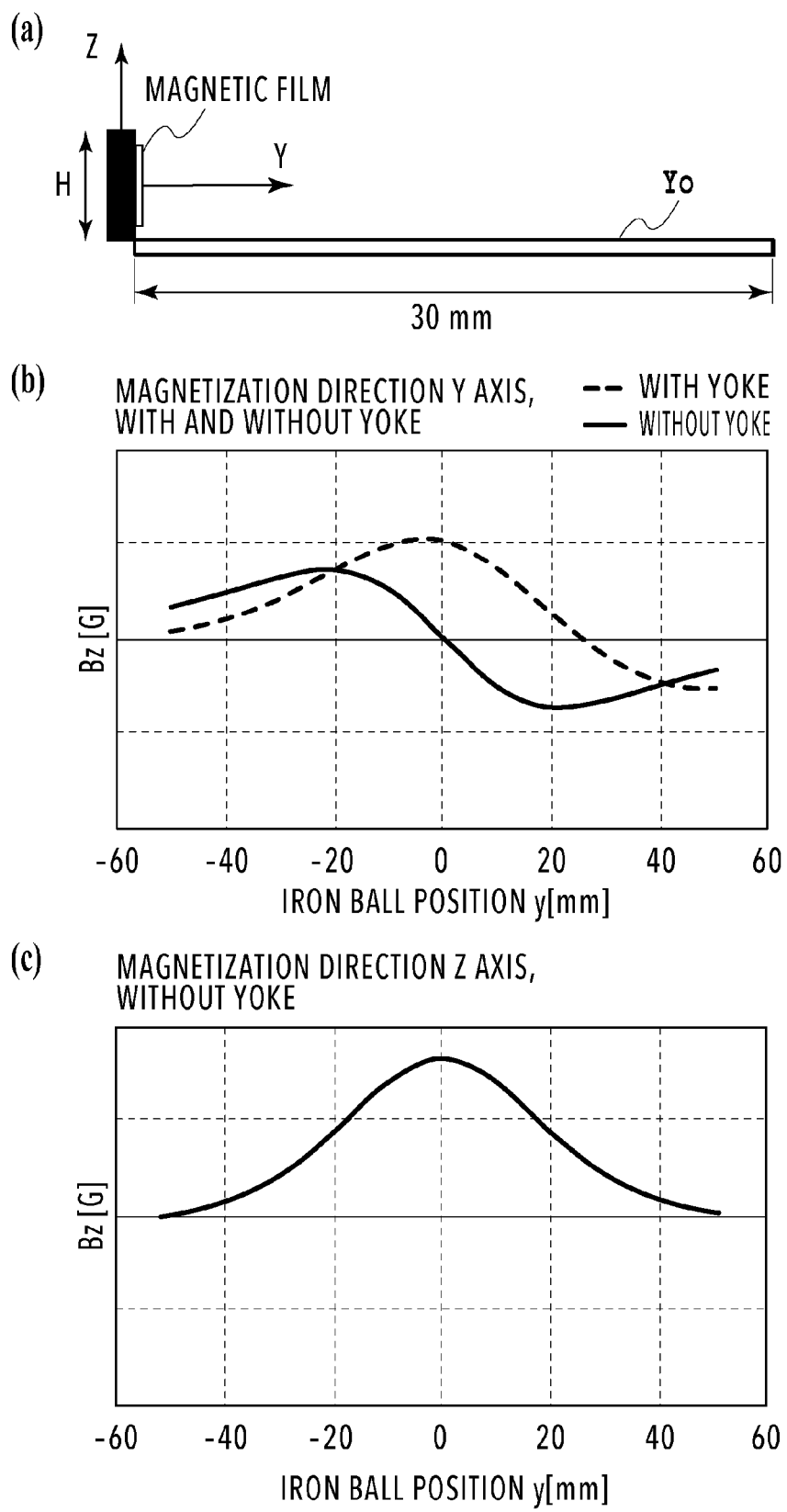
FIG. 23 illustrates a magnetic sensor and graphs of detection signals.

As an example, assume a case where a yoke Yo with a length of 30 mm is arranged downstream of the magnetic sensor MS in the conveyance direction (Y direction) as illustrated in part (a) of FIG. 23. Part (b) of FIG. 23 illustrates simulation results of detection signal waveforms obtained in the case where a magnetization direction of an iron ball that is an example of the magnetic foreign object is orthogonal to the magnetic field detection direction of the magnetic sensor MS, the respective waveforms corresponding to the case where the yoke Yo is provided and the case where no yoke Yo is provided. Note that an iron ball position y in the graphs illustrated in FIG. 23 is based on the position of the magnetic sensor MS in the conveyance direction.

The iron ball is magnetized in the Y direction to set the magnetizing direction of the iron ball orthogonal to the magnetic field detection direction of the magnetic sensor MS. In the case where no yoke Yo is provided, the polarity of the waveform of the detection signal reverses at the position of the magnetic sensor MS as illustrated by the solid line in part (b) of FIG. 23. This is because the direction of a Z-direction component of the magnetic field generated by the iron ball in the magnetic sensor MS reverses at the position of the magnetic sensor MS.

Meanwhile, in the case where the yoke Yo is provided, the waveform of the detection signal has a peak near the position of the magnetic sensor MS as illustrated by the broken line in part (b) of FIG. 23 and has a shape close to an ideal waveform illustrated in part (c) of FIG. 23, which is obtained in the case where the magnetic field detection direction of the magnetic sensor MS coincides with the magnetizing direction of the iron ball. This is because magnetic flux passing the yoke Yo flows from a left end portion of the yoke Yo in part (a) of FIG. 23 toward the magnetic sensor MS to be guided to a magnetic film in a magnetic sensing unit and the magnetic sensor MS detects the magnetic field.

Figure 24:
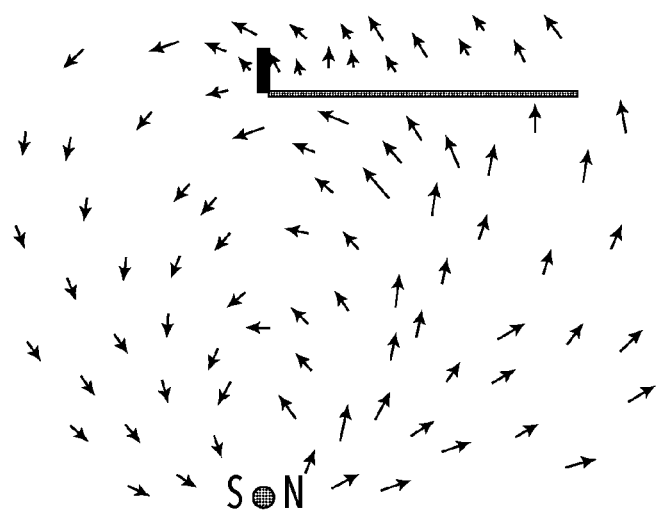
FIG. 24 includes diagrams illustrating the magnetic sensor and flows of magnetic flux.
Figure 24:
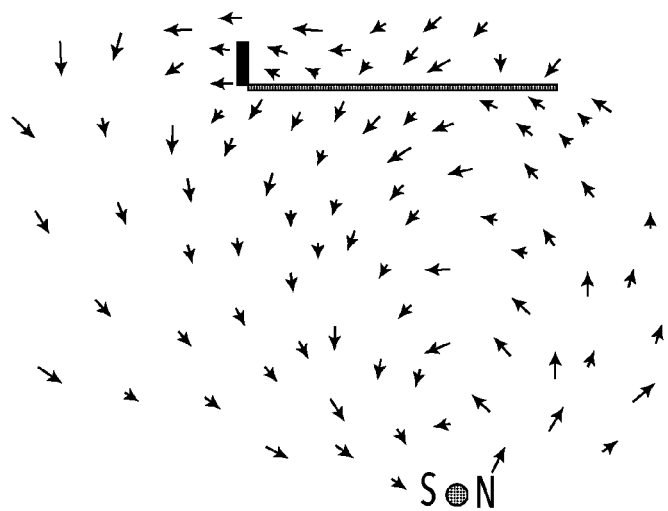
Figure 24:
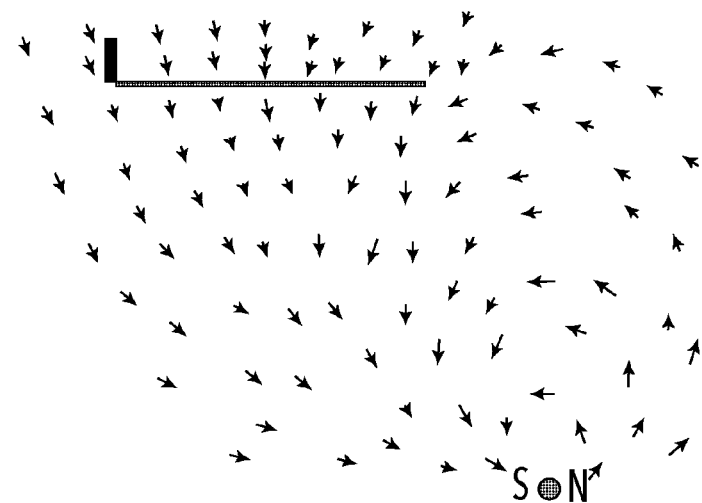

In the case where the iron ball is upstream (y<0) of the magnetic sensor MS, the magnetic sensor MS mainly detect a magnetic field generated by the magnetic flux from the iron ball. In the case where the iron ball comes close to the magnetic sensor MS (y≈0) (part (a) of FIG. 24), the magnetic flux directly reaching the magnetic sensing unit in the magnetic sensor MS from the iron ball decrease but the magnetic flux passes the yoke Yo to be guided from the left end portion of the yoke Yo to the magnetic sensing unit. The magnetic sensor MS detects the magnetic flux flowing from the left end portion of the yoke Yo to the magnetic sensing unit. In this case, the direction of the magnetic flux passing the magnetic sensing unit in the magnetic sensor MS relative to the Z direction does not change and the polarity of the detecting signal waveform thus also does not change. Even if the iron ball moves downstream (y>0) of the magnetic sensor MS from this position, the magnetization direction of the yoke Yo is maintained substantially in the leftward direction (part (b) of FIG. 24). Components guided from the left end portion of the yoke Yo to the magnetic sensing unit in the magnetic sensor MS are still left and the polarity of the detection signal waveform is maintained. In the case where the iron ball moves further downstream (part (c) of FIG. 24), the magnetic flux flowing from the left end portion of the yoke Yo to the magnetic sensing unit in the magnetic sensor MS decrease. In part (c) of FIG. 24, there is no magnetic flux flowing from the left end portion of the yoke Yo to the magnetic sensing unit in the magnetic sensor MS and magnetic flux in the opposite direction passes the magnetic sensing unit in the magnetic sensor MS. Specifically, the direction of the magnetic flux relative to the Z direction reverses and the polarity of the detection signal waveform also reverses.

This case describes the case where the magnetizing direction is tilted to the greatest extent. In actual, the magnetization direction is not tilted to this extent and the waveform is closer to that illustrated in part (c) of FIG. 23 than that illustrated by the broken line in part (b) of FIG. 23. Specifically, it is possible to suppress reversal of the polarity and increase the strength of the detected magnetic field from those in the case where no yoke Yo is provided.

Since the yoke Yo arranged close to the magnetic sensor MS as described above has a phase adjusting effect of suppressing the change in the direction of the magnetic field detected by the magnetic sensor MS, the yoke Yo can suppress turning of the phase of the detection signal waveform in the case where the magnetization direction of the magnetic foreign object is different from the magnetic field detection direction of the magnetic sensor MS. Accordingly, in the embodiment, changes in the magnetic field caused by moving of the magnetic foreign object can be more accurately detected, irrespective of the magnetization direction of the magnetic foreign object. The phase adjustment effect obtained by arranging the yoke Yo can be similarly obtained also in the case where the multiplication processing is performed on the signals of the magnetic detectors arranged above and below the conveyance route as a matter of course.

Note that the angle θ formed between the yoke Yo and the magnetic field detection direction of the magnetic sensor MS illustrated in part (b) of FIG. 22 may be any angle. However, since the detection sensitivity of the magnetic sensor decreases due to a shielding effect in the case where the angle θ is 0 degrees to 90 degrees, the angle θ is preferably 90 degrees to 180 degrees. The end portion of the yoke Yo is preferably arranged close to an end portion of the magnetic sensing unit in the magnetic sensor MS and a magnetic sensing surface of the sensor and the end portion of the yoke Yo are preferably aligned with each other in the Y direction. Moreover, setting the distance between the magnetic sensing surface and the end portion in the Z direction smaller is more preferable. The magnetic sensing surface of the sensor and the yoke Yo may be in contact with each other.

Figure 25:
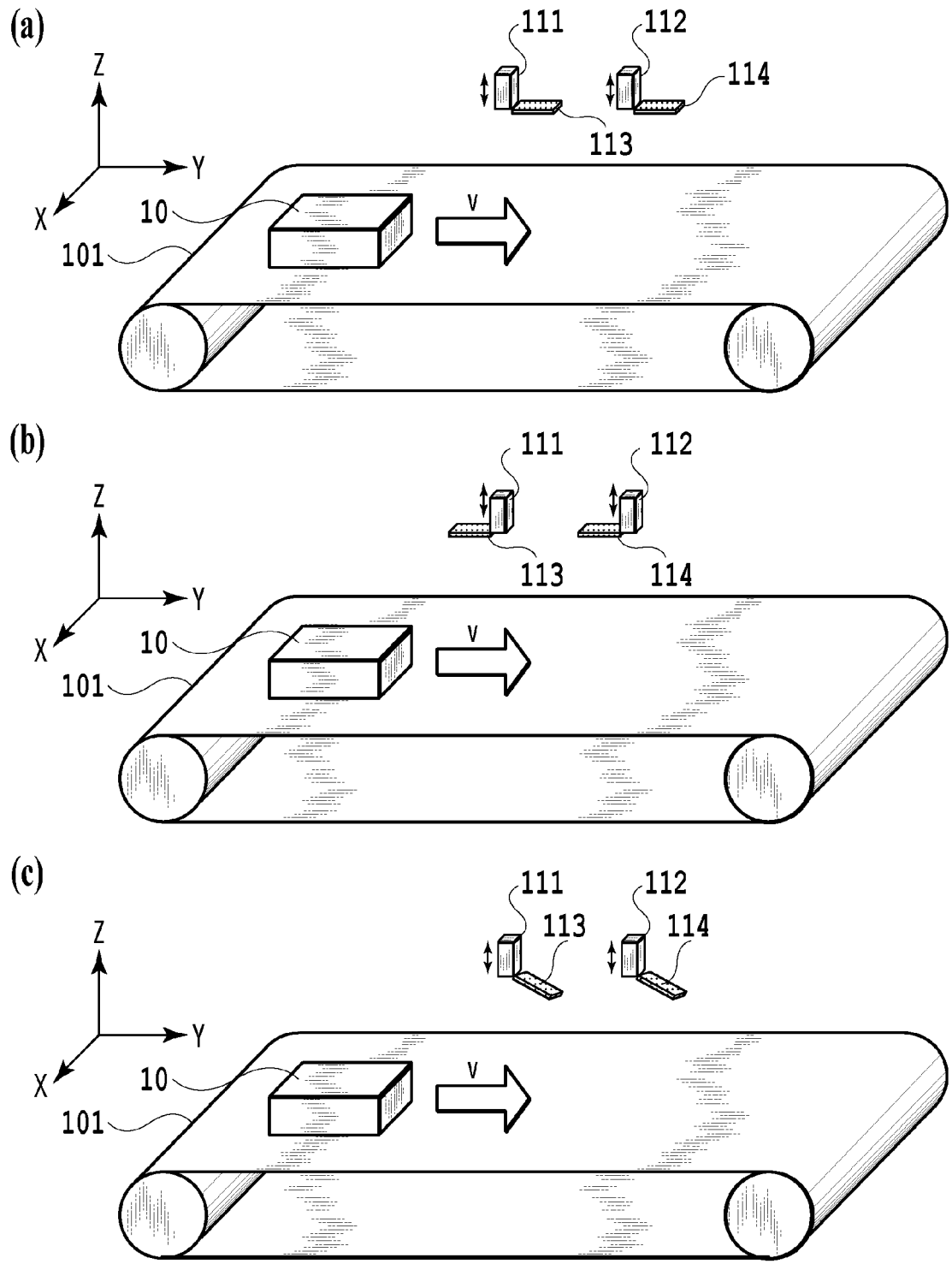
FIG. 25 is a schematic configuration diagram illustrating arrangement examples of yokes in the inspection device according to the eighth embodiment of the present invention.

FIG. 25 illustrates arrangement examples of yokes in a configuration including paired magnetic detectors on one side of the conveyance route. The yokes 113, 114 may be arranged such that their longitudinal directions coincide with the conveyance direction (Y direction) as illustrated in parts (a) and (b) of FIG. 25 or such that their longitudinal directions are tilted to the width direction with respect to the conveyance direction as illustrated in part (c) of FIG. 25. Moreover, the yokes 113, 114 may be arranged upstream or downstream of the magnetic detectors. In the case where the yokes are arranged in the same direction with respect to the conveyance direction (Y direction) of the inspection object 10 for the magnetic detectors whose detection signals are to be subjected to the differential processing, the disturbance noises detected by the first magnetic detector 111 and the second magnetic detector 112 have the same phase and the removal of the noise is thus simplified in the configuration in which the differential processing is performed.

Figure 26:
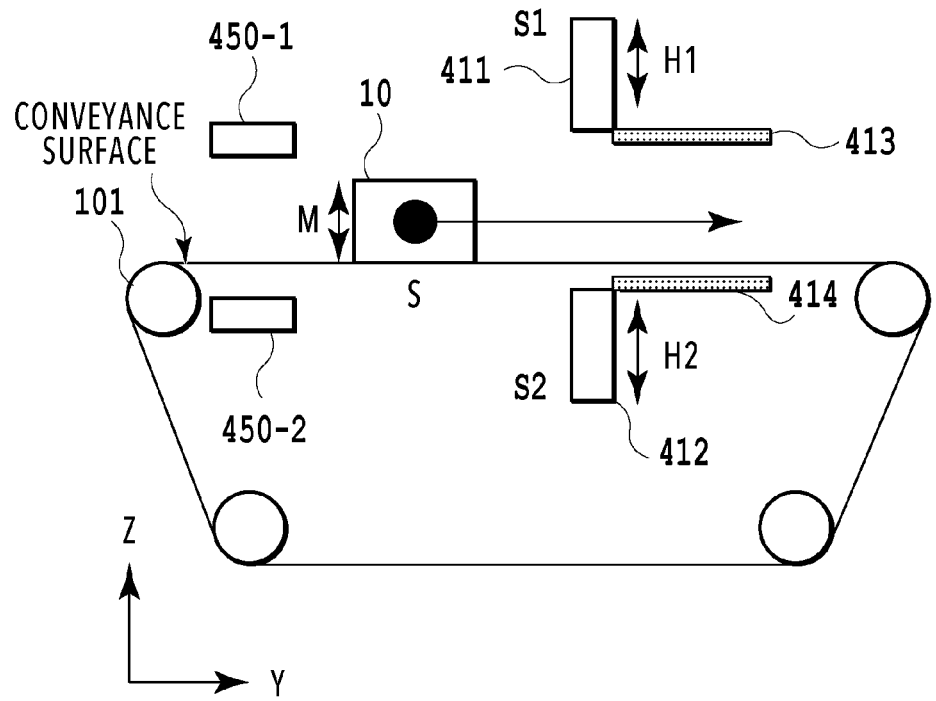
FIG. 26 is a schematic configuration diagram illustrating arrangement examples of yokes in the inspection device according to the eighth embodiment of the present invention.
Figure 26:
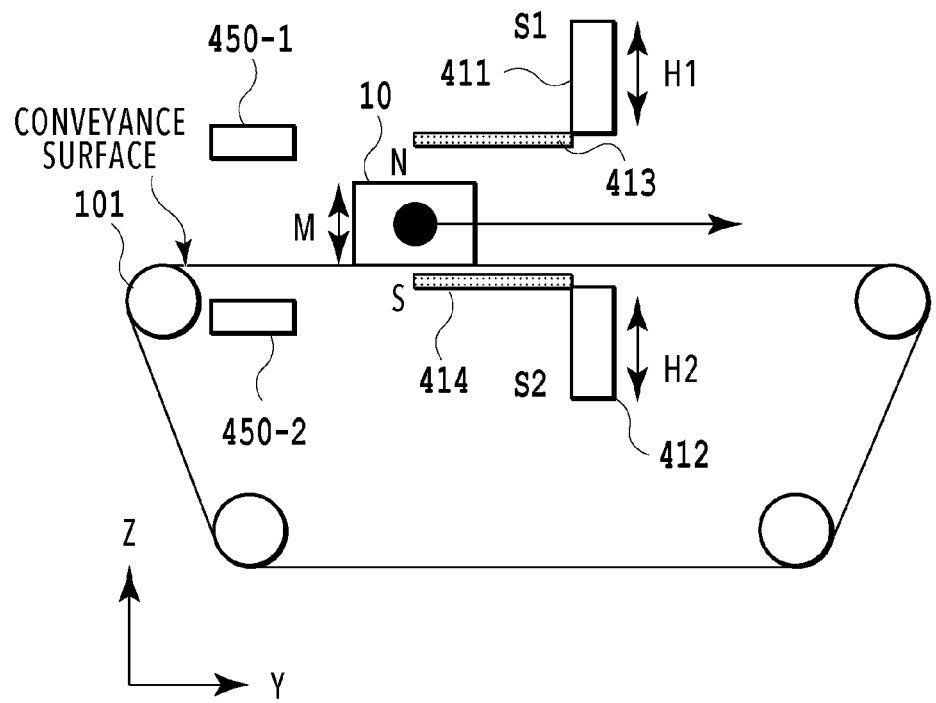
Figure 27:
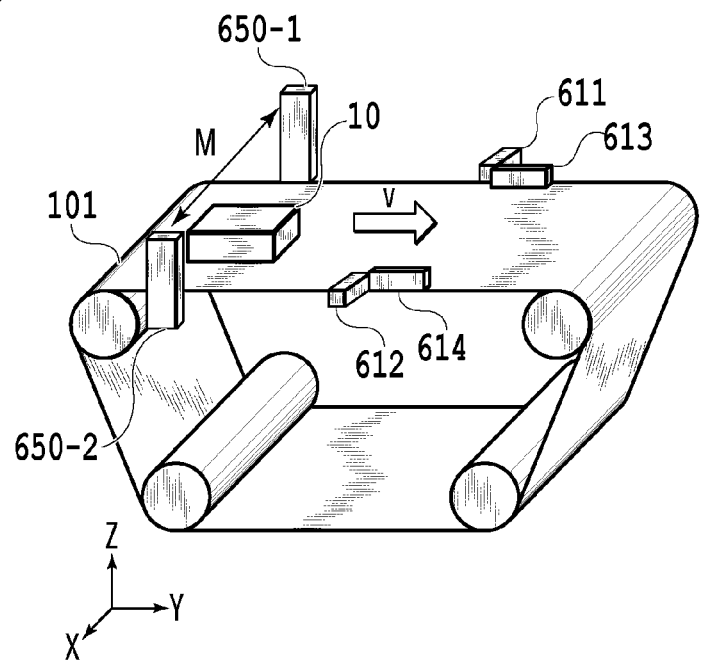
FIG. 27 is a schematic configuration diagram illustrating arrangement examples of yokes in the inspection device according to the eighth embodiment of the present invention.
Figure 27:
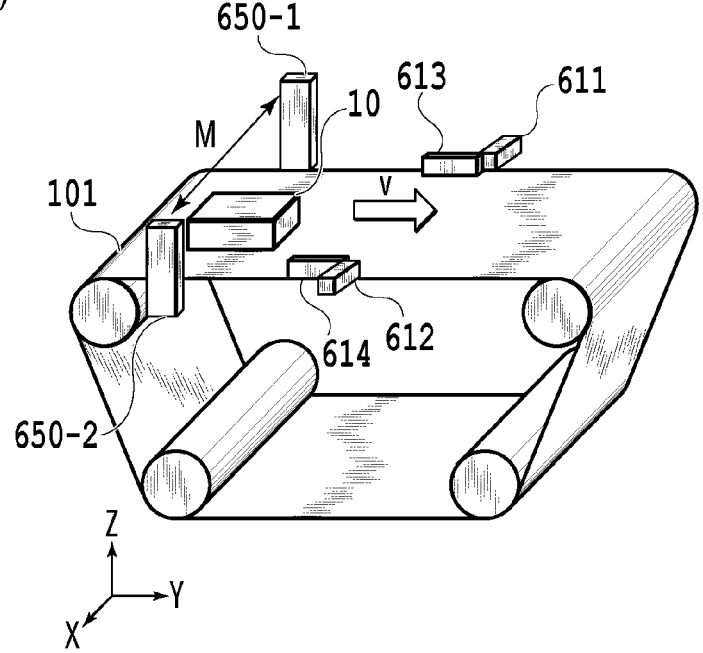

FIG. 26 illustrates arrangement examples of yokes in a configuration including paired magnetic detectors above and below the conveyance route. Moreover, FIG. 27 illustrates arrangement examples of yokes in a configuration including paired magnetic detectors on both sides of the conveyance route in the width direction. Also in these cases, the yokes only need to be arranged as in the configuration including paired magnetic detectors on one side of the conveyance route.

Note that, although the yoke Yo is arranged at the lower end (negative end portion in the Z direction) of the magnetic sensor MS in the embodiment, the yoke Yo may be arranged at an upper end (positive end portion in the Z direction). However, in the case where the yoke Yo is arranged on the lower end side of the magnetic sensor MS as in the embodiment, more magnetic flux passes through the yoke Yo and the effect of the present invention can be effectively obtained.

A high magnetic permeability material such as permalloy or silicon steel plate may be used for a member of the yoke Yo. The yoke may have a quadrilateral shape such as a square or rectangular shape or may have a comb shape. The narrower the shape of the end portion of yoke away from the magnetic sensor is, the higher the obtained effect is. This is due to a relationship with demagnetizing field. The width of the yoke may be greater than the width of the magnetic sensing unit in the magnetic sensor.

The present invention is not limited to the aforementioned embodiments and various changes can be made within the scope of a technical idea of the present invention. The aforementioned embodiments may be used in combination. For example, the configuration may be such that the upper magnetic detector 411 and the lower magnetic detector 412 are each formed of one magnetic sensor as in the fifth embodiment and the magnetic shielding unit 440 is provided to cover each of the sensors.

Moreover, the multiplication of the signals in the present invention is not limited to the multiplication of two detection signals obtained from paired magnetic detectors and may be multiplication of three or more detection signals obtained from three or more magnetic detectors. In the configuration in which the magnetic detectors are arranged respectively on the upstream side and the downstream side in the conveyance direction as in the first to fourth embodiments, another magnetic detector may be further provided downstream of these detectors. In the configuration in which the magnetic detectors are arranged above and below the conveyance route as in the fifth to seventh embodiments, for example, two magnetic detectors arranged one on top of the other may be provided as the magnetic detector in a lower stage.

Furthermore, in the present invention, the configuration may be such that a peak is detected from the detected waveform and multiplication processing by the multiplication processing unit is performed before and after the peak.

Moreover, in the present invention, after the multiple detection signals are multiplied, computation with another function such as the template waveform of Patent Literature 1 may be additionally performed.

Although the noise components generated by disturbance magnetic field are given as an example of the noise in the description of the present invention, the noise includes noise generated in the magnetic sensors, other sensors, and a circuit board.

REFERENCE SIGNS LIST 10 inspection object
100 inspection device
101 conveyance route
111, 112 magnetic detector
120 amplifying unit
130 computation processing unit
131 AD convertor
132 multiplication processing unit
133 determination unit
140 magnetic shielding unit
150 magnetizing unit

The invention claimed is:

1. An inspection device comprising:
a conveyor configured to convey an inspection object along a conveyance route;
a plurality of magnetic detectors configured to detect a magnetic field generated by remanent magnetization of a magnetic foreign object contained in the inspection object; and
a computer configured to perform processing of multiplying one detection signal of the plurality of magnetic detectors by another detection signal of the plurality of magnetic detectors,
wherein the computer is configured to perform processing of multiplying the detection signals for the same inspection object conveyed by the conveyor together.

2. The inspection device according to claim 1, wherein the plurality of magnetic detectors detect a component, in a direction perpendicular to a conveyance surface of the conveyor, of the magnetic field generated by the remanent magnetization and are arranged at a predetermined interval in a conveyance direction of the conveyor, and
wherein the computer performs time correction on at least one of the detection signals before the multiplication processing such that timings at which the inspection object comes closest to the respective magnetic detectors substantially match each other in the respective detection signals.

3. The inspection device according to claim 2, wherein the computer performs the time correction on the detection signal such that the detection signal is delayed by a time difference corresponding to time the conveyor takes to convey the inspection object over the predetermined interval.

4. The inspection device according to claim 2, wherein the predetermined interval and conveyance speed of the conveyor are set such that, in the case where the plurality of magnetic detectors detect a disturbance noise signal that has a predetermined frequency component and is included in a noise signal detected by the plurality of magnetic detectors, a phase of the disturbance noise signal detected in one of the plurality of magnetic detectors is opposite to that in another magnetic detector.

5. The inspection device according to claim 4, wherein the predetermined interval is a value obtained by multiplying a value odd-number times a half period of the disturbance noise signal by the conveyance speed.

6. The inspection device according to claim 4, wherein the predetermined frequency component is a frequency different from a frequency of a signal component detecting the magnetic foreign object contained in the inspection object, with the frequency of the signal component defined by the conveyance speed.

7. The inspection device according to claim 1, wherein the plurality of magnetic detectors are arranged to face each other with the conveyance route therebetween and detect a component, in a direction perpendicular to a conveyance surface of the conveyor, of the magnetic field generated by the remanent magnetization.

8. The inspection device according to claim 1, wherein at least one of the plurality of magnetic detectors includes a plurality of magnetic sensors arranged in a width direction of the conveyance route.

9. The inspection device according to claim 8, wherein presence or absence of the magnetic foreign object and a passing position of the magnetic foreign object in the width direction of the conveyance route are determined from a result of the multiplication processing by the computer.

10. The inspection device according to claim 1, wherein the plurality of magnetic detectors are arranged at both ends of the conveyance route in a width direction to face each other with the conveyance route therebetween and detect a component, in the width direction of the conveyance route, of the magnetic field generated by the remanent magnetization.

11. The inspection device according to claim 10, wherein the plurality of magnetic detectors include a plurality of magnetic sensors arranged in a direction perpendicular to a conveyance surface of the conveyor.

12. The inspection device according to claim 1, wherein the plurality of magnetic detectors includes magnetic sensors having magnetic field detection directions parallel to each other.

13. The inspection device according to claim 1, wherein the computer performs level correction on the detection signals before the multiplication processing.

14. The inspection device according to claim 13, wherein the computer performs the level correction such that an average value of each of the detection signals in a period where the inspection object containing the magnetic foreign object is absent on the conveyance route is set as zero.

15. The inspection device according to claim 1, wherein the computer performs the multiplication processing by using signals obtained by performing differential processing on the detection signals detected at the same timing as the detection signals.

16. The inspection device according to claim 1, wherein the inspection device further comprises a phase adjusting unit arranged in an end portions of each of the plurality of magnetic detectors.

17. The inspection device according to claim 16, wherein the phase adjusting unit contains a high magnetic permeability material.

18. The inspection device according to claim 16, wherein the phase adjusting unit is arranged such that a longitudinal direction of the phase adjusting unit coincides with a conveyance direction of the conveyor.

19. The inspection device according to claim 16, wherein an angle formed between a magnetic field detection direction of each of the magnetic detectors and a longitudinal direction of the phase adjusting unit is 90 degrees to 180 degrees.

20. The inspection device according to claim 1, wherein the inspection device further comprises magnetizing unit configured to magnetize the magnetic foreign object contained in the inspection object, the magnetizing unit provided upstream of the plurality of the magnetic detectors in a conveyance direction of the conveyor.

21. The inspection device according to claim 1, wherein the inspection device further comprises magnetic shielding unit configured to cover each of the plurality of the magnetic detectors, the magnetic shielding unit being open on a surface facing the conveyor.

22. The inspection device according to claim 1, wherein the inspection device further comprises a determination unit configured to determine that the inspection object contains the magnetic foreign object in the case where a multiplication result calculated by the computer is equal to or greater than a predetermined value.

23. The inspection device according to claim 22, wherein the determination unit determines at least a signal component with an opposite phase to a signal component detecting the magnetic foreign object as a noise component generated by a disturbance magnetic field.

24. The inspection device according to claim 1, wherein the inspection device includes a display unit configured to display a waveform in which a signal component detecting the magnetic foreign object with respect to the inspection object has a positive value equal to or greater than a predetermined value and a signal component detecting only noise has a negative value, based on a result of the multiplication processing by the computer.

* * * * *